US011865407B1

(12) United States Patent
Berme et al.

(10) Patent No.: US 11,865,407 B1
(45) Date of Patent: Jan. 9, 2024

(54) MEASUREMENT AND TESTING SYSTEM

(71) Applicant: Bertec Corporation, Columbus, OH (US)

(72) Inventors: Necip Berme, Worthington, OH (US); Murat Kerim Berme, Venice, CA (US); Fernando Vanderlinde dos Santos, Columbus, OH (US); Geoffrey Lee Brown, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 18/077,037

(22) Filed: Dec. 7, 2022

Related U.S. Application Data

(60) Provisional application No. 63/399,191, filed on Aug. 18, 2022.

(51) Int. Cl.
  *A63B 24/00* (2006.01)
  *A63B 22/02* (2006.01)
  *A63B 71/06* (2006.01)

(52) U.S. Cl.
  CPC ........ *A63B 24/0062* (2013.01); *A63B 22/025* (2015.10); *A63B 71/0622* (2013.01); *A63B 2024/0093* (2013.01)

(58) Field of Classification Search
  CPC ............. A63B 24/0062; A63B 22/025; A63B 71/0622; A63B 2024/0093
  USPC ....................................................... 700/173
  See application file for complete search history.

(56) References Cited

U.S. PATENT DOCUMENTS

| | | | |
|---|---|---|---|
| 6,038,488 A | 3/2000 | Barnes et al. |
| 6,113,237 A | 9/2000 | Ober et al. |
| 6,152,564 A | 11/2000 | Ober et al. |
| 6,295,878 B1 | 10/2001 | Berme |
| 6,354,155 B1 | 3/2002 | Berme |
| 6,389,883 B1 | 5/2002 | Berme et al. |
| 6,936,016 B2 | 8/2005 | Berme et al. |
| 8,181,541 B2 | 5/2012 | Berme |
| 8,315,822 B2 | 11/2012 | Berme et al. |
| 8,315,823 B2 | 11/2012 | Berme et al. |
| D689,388 S | 9/2013 | Berme |
| D689,389 S | 9/2013 | Berme |
| 8,543,540 B1 | 9/2013 | Wilson et al. |
| 8,544,347 B1 | 10/2013 | Berme |
| 8,643,669 B1 | 2/2014 | Wilson et al. |

(Continued)

*Primary Examiner* — Michael J Brown
(74) *Attorney, Agent, or Firm* — The Law Office of Patrick F. O'Reilly III, LLC

(57) ABSTRACT

A measurement and testing system is disclosed herein. The measurement and testing system includes at least one data processing device operatively coupled to at least one actuator, a visual display device, and a user input device. The at least one data processing device being configured to execute computer executable stored instructions for: (i) generating a graphical user interface with a protocol section comprising one or more protocols with one or more actuator parameters for controlling the at least one actuator for a time period; (ii) receiving an input signal from the user input device that initiates an execution of one of the one or more protocols for controlling the at least one actuator; and (iii) upon receiving the input signal from the user input device, controlling the at least one actuator for the time period in accordance with the executed one of the one or more protocols.

26 Claims, 8 Drawing Sheets

(56) References Cited

U.S. PATENT DOCUMENTS

| | | |
|---|---|---|
| 8,700,569 B1 | 4/2014 | Wilson et al. |
| 8,704,855 B1 | 4/2014 | Berme et al. |
| 8,764,532 B1 | 7/2014 | Berme |
| 8,847,989 B1 | 9/2014 | Berme et al. |
| D715,669 S | 10/2014 | Berme |
| 8,902,249 B1 | 12/2014 | Wilson et al. |
| 8,915,149 B1 | 12/2014 | Berme |
| 9,032,817 B2 | 5/2015 | Berme et al. |
| 9,043,278 B1 | 5/2015 | Wilson et al. |
| 9,066,667 B1 | 6/2015 | Berme et al. |
| 9,081,436 B1 | 7/2015 | Berme et al. |
| 9,168,420 B1 | 10/2015 | Berme et al. |
| 9,173,596 B1 | 11/2015 | Berme et al. |
| 9,200,897 B1 | 12/2015 | Wilson et al. |
| 9,277,857 B1 | 3/2016 | Berme et al. |
| D755,067 S | 5/2016 | Berme et al. |
| 9,404,823 B1 | 8/2016 | Berme et al. |
| 9,414,784 B1 | 8/2016 | Berme et al. |
| 9,468,370 B1 | 10/2016 | Shearer |
| 9,517,008 B1 | 12/2016 | Berme et al. |
| 9,526,443 B1 | 12/2016 | Berme et al. |
| 9,526,451 B1 | 12/2016 | Berme |
| 9,558,399 B1 | 1/2017 | Jeka et al. |
| 9,568,382 B1 | 2/2017 | Berme et al. |
| 9,622,686 B1 | 4/2017 | Berme et al. |
| 9,763,604 B1 | 9/2017 | Berme et al. |
| 9,770,203 B1 | 9/2017 | Berme et al. |
| 9,778,119 B2 | 10/2017 | Berme et al. |
| 9,814,430 B1 | 11/2017 | Berme et al. |
| 9,829,311 B1 | 11/2017 | Wilson et al. |
| 9,854,997 B1 | 1/2018 | Berme et al. |
| 9,916,011 B1 | 3/2018 | Berme et al. |
| 9,927,312 B1 | 3/2018 | Berme et al. |
| 10,010,248 B1 | 7/2018 | Shearer |
| 10,010,286 B1 | 7/2018 | Berme et al. |
| 10,085,676 B1 | 10/2018 | Berme et al. |
| 10,117,602 B1 | 11/2018 | Berme et al. |
| 10,126,186 B2 | 11/2018 | Berme et al. |
| 10,216,262 B1 | 2/2019 | Berme et al. |
| 10,231,662 B1 | 3/2019 | Berme et al. |
| 10,264,964 B1 | 4/2019 | Berme et al. |
| 10,331,324 B1 | 6/2019 | Wilson et al. |
| 10,342,473 B1 | 7/2019 | Berme et al. |
| 10,390,736 B1 | 8/2019 | Berme et al. |
| 10,413,230 B1 | 9/2019 | Berme et al. |
| 10,463,250 B1 | 11/2019 | Berme et al. |
| 10,527,508 B2 | 1/2020 | Berme et al. |
| 10,555,688 B1 | 2/2020 | Berme et al. |
| 10,646,153 B1 | 5/2020 | Berme et al. |
| 10,722,114 B1 | 7/2020 | Berme et al. |
| 10,736,545 B1 | 8/2020 | Berme et al. |
| 10,765,936 B2 | 9/2020 | Berme et al. |
| 10,803,990 B1 | 10/2020 | Wilson et al. |
| 10,853,970 B1 | 12/2020 | Akbas et al. |
| 10,856,796 B1 | 12/2020 | Berme et al. |
| 10,860,843 B1 | 12/2020 | Berme et al. |
| 10,945,599 B1 | 3/2021 | Berme et al. |
| 10,966,606 B1 | 4/2021 | Berme |
| 11,033,453 B1 | 6/2021 | Berme et al. |
| 11,052,288 B1 | 7/2021 | Berme et al. |
| 11,054,325 B2 | 7/2021 | Berme et al. |
| 11,074,711 B1 | 7/2021 | Akbas et al. |
| 11,097,154 B1 | 8/2021 | Berme et al. |
| 11,158,422 B1 | 10/2021 | Wilson et al. |
| 11,182,924 B1 | 11/2021 | Akbas et al. |
| 11,262,231 B1 | 3/2022 | Berme et al. |
| 11,262,258 B2 | 3/2022 | Berme et al. |
| 11,301,045 B1 | 4/2022 | Berme et al. |
| 11,311,209 B1 | 4/2022 | Berme et al. |
| 11,321,868 B1 | 5/2022 | Akbas et al. |
| 11,337,606 B1 | 5/2022 | Berme et al. |
| 11,348,279 B1 | 5/2022 | Akbas et al. |
| 11,458,362 B1 | 10/2022 | Berme et al. |
| 11,521,373 B1 | 12/2022 | Akbas et al. |
| 11,540,744 B1 | 1/2023 | Berme |
| 2003/0216656 A1 | 11/2003 | Berme et al. |
| 2008/0228110 A1 | 9/2008 | Berme |
| 2011/0277562 A1 | 11/2011 | Berme |
| 2012/0266648 A1 | 10/2012 | Berme et al. |
| 2012/0271565 A1 | 10/2012 | Berme et al. |
| 2015/0096387 A1 | 4/2015 | Berme et al. |
| 2016/0245711 A1 | 8/2016 | Berme et al. |
| 2016/0334288 A1 | 11/2016 | Berme et al. |
| 2018/0024015 A1 | 1/2018 | Berme et al. |
| 2019/0078951 A1 | 3/2019 | Berme et al. |
| 2020/0139229 A1 | 5/2020 | Berme et al. |
| 2020/0408625 A1 | 12/2020 | Berme et al. |
| 2021/0333163 A1 | 10/2021 | Berme et al. |
| 2022/0143462 A1* | 5/2022 | Velo ............... A61B 5/6895 |
| 2022/0178775 A1 | 6/2022 | Berme et al. |

* cited by examiner

FIG. 3

MEASUREMENT AND TESTING SYSTEM

CROSS-REFERENCE TO RELATED APPLICATIONS

This patent application claims priority to, and incorporates by reference in its entirety, U.S. Provisional Patent Application No. 63/399,191, entitled "Measurement And Testing System", filed on Aug. 18, 2022.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a measurement and testing system. More particularly, the invention relates to a measurement and testing system with a graphical user interface that enables a user to execute and customize protocols for controlling one or more devices of the measurement and testing system.

2. Background

Measurement and testing systems are utilized in various fields to detect and analyze many different measurable quantities. For example, in biomedical applications, measurement and testing systems are used for gait analysis, assessing balance and mobility, evaluating sports performance, and assessing ergonomics. However, conventional measurement and testing systems have numerous limitations and drawbacks.

Because a typical data acquisition and/or analysis software program is often utilized by end users having a large variety of different testing and/or training needs, ideally the program would be easily customizable to suit these various needs. However, conventional data acquisition and/or analysis software programs are written in a complex software programming language that is rarely understandable to the end users of the measurement and testing system. As such, because the end users are not fluent in the specialized programming language in which the program is written, they are unable to modify the software program in order to suit their specific needs (e.g., they are unable to develop a customized test and/or training routine). Also, a conventional data acquisition and/or analysis software program often requires a substantial amount of repetitive manual data entry by the end user in order to execute a desired test and/or training routine.

Therefore, what is needed is a measurement and testing system with a graphical user interface that enables an end user to easily customize and execute protocols for controlling one or more devices of the measurement and testing system without unnecessary repetitive manual data entry.

BRIEF SUMMARY OF EMBODIMENTS OF THE INVENTION

Accordingly, the present invention is directed to a measurement and testing system that substantially obviates one or more problems resulting from the limitations and deficiencies of the related art.

In accordance with one or more embodiments of the present invention, there is provided a measurement and testing system that comprises at least one actuator, the at least one actuator configured to displace a surface on which a subject is disposed; a visual display device having an output screen; a user input device, the user input device configured to enable a user of the system to input or manipulate data; and at least one data processing device operatively coupled to the at least one actuator, the visual display device, and the user input device. The at least one data processing device including at least one hardware component, and the at least one data processing device configured to execute computer executable stored instructions. The computer executable stored instructions comprising instructions for: (i) generating a graphical user interface on the output screen of the visual display device, the graphical user interface including a protocol section, the protocol section comprising one or more protocols with one or more actuator parameters for controlling the at least one actuator for a time period while the subject is disposed on the surface; (ii) receiving an input signal from the user input device that initiates an execution of one of the one or more protocols for controlling the at least one actuator; and (iii) upon receiving the input signal from the user input device, controlling the at least one actuator for the time period in accordance with the executed one of the one or more protocols so as to displace the surface on which the subject is disposed in a prescribed manner.

In a further embodiment of the present invention, at least one of the one or more protocols displayed in the protocol section of the graphical user interface further comprises one or more device responses for automatically controlling the at least one actuator for the time period, each of the one or more device responses including a start time and an end time.

In yet a further embodiment, the at least one actuator further comprises at least one first actuator of a first device and at least one second actuator of a second device, and the one or more device responses further comprise a first device response for automatically controlling the first actuator of the first device and a second device response for automatically controlling the second actuator of the second device.

In still a further embodiment, the first device response and the second device response are executed simultaneously such that the first device and the second device are simultaneously displaced during a single predetermined time period.

In yet a further embodiment, the first device response and the second device response are executed sequentially such that the first device undergoes displacement initially during a first predetermined time period, followed by displacement of the second device during a second predetermined time period.

In still a further embodiment, the first device is an instrumented treadmill and the at least one first actuator is an electric motor for rotating one or more belts of the instrumented treadmill; and the second device is a motion base and the at least one second actuator is a motion base actuator for displacing the motion base.

In yet a further embodiment, the at least one actuator further comprises at least one first actuator of a device and at least one second actuator of the device, and the one or more device responses further comprise a first device response for automatically controlling the first actuator of the device and a second device response for automatically controlling the second actuator of the device.

In still a further embodiment, the first device response and the second device response are executed simultaneously such that the device is simultaneously displaced by the at least one first actuator and the at least one second actuator during a single predetermined time period.

In yet a further embodiment, the first device response and the second device response are executed sequentially such that the device undergoes displacement from the at least one first actuator initially during a first predetermined time period, followed by displacement from the at least one second actuator during a second predetermined time period.

In still a further embodiment, the device is an instrumented treadmill with incline adjustment and the at least one first actuator is an electric motor for rotating one or more belts of the instrumented treadmill and the at least one second actuator is a treadmill incline actuator for adjusting an inclination angle of the instrumented treadmill.

In yet a further embodiment, at least one of the one or more protocols displayed in the protocol section of the graphical user interface further comprises a plurality of protocols arranged in a queue, and the at least one data processing device is further configured to execute computer executable stored instructions for: (iv) receiving an input signal from the user input device that initiates an execution of a first one of the plurality of protocols arranged in the queue; and (v) after completing the first one of the plurality of protocols, automatically executing each successive one of the plurality of protocols arranged in the queue.

In still a further embodiment, the measurement and testing system further comprises a measurement assembly having at least one measurement device, the at least one measurement device being configured to sense one or more measured quantities and output one or more signals that are representative of the one or more measured quantities, the at least one data processing device being further operatively coupled to the at least one measurement device of the measurement assembly, and the at least one data processing device being further configured to execute computer executable stored instructions for: (iv) receiving the one or more signals that are representative of the one or more measured quantities and converting the one or more signals into output data; and (v) displaying the output data in a portion of the graphical user interface on the output screen of the visual display device.

In yet a further embodiment, the at least one data processing device is further configured to synchronize a capture of the output data from the at least one measurement device of the measurement assembly with the execution of the one of the one or more protocols resulting in a displacement of the surface on which the subject is disposed.

In accordance with one or more other embodiments of the present invention, there is provided a measurement and testing system that comprises a measurement assembly having at least one measurement device, the at least one measurement device configured to sense one or more measured quantities and output one or more signals that are representative of the one or more measured quantities; at least one actuator, the at least one actuator configured to displace a surface on which a subject is disposed; a visual display device having an output screen; a user input device, the user input device configured to enable a user of the system to input or manipulate data; and at least one data processing device operatively coupled to the at least one measurement device of the measurement assembly, the at least one actuator, the visual display device, and the user input device. The at least one data processing device including at least one hardware component, and the at least one data processing device configured to execute computer executable stored instructions. The computer executable stored instructions comprising instructions for: (i) generating a graphical user interface on the output screen of the visual display device, the graphical user interface including a protocol section, the protocol section comprising one or more protocols with one or more actuator parameters for controlling the at least one actuator for a time period while the subject is disposed on the surface; (ii) receiving an input signal from the user input device that initiates an execution of one of the one or more protocols for controlling the at least one actuator; (iii) upon receiving the input signal from the user input device, controlling the at least one actuator for the time period in accordance with the executed one of the one or more protocols so as to displace the surface on which the subject is disposed in a prescribed manner; (iv) receiving the one or more signals that are representative of the one or more measured quantities and converting the one or more signals into output data; and (v) displaying the output data in a portion of the graphical user interface on the output screen of the visual display device.

In a further embodiment of the present invention, at least one of the one or more protocols displayed in the protocol section of the graphical user interface further comprises one or more device responses for automatically controlling the at least one actuator for the time period, each of the one or more device responses including a start time and an end time.

In yet a further embodiment, the at least one actuator further comprises at least one first actuator of a first device and at least one second actuator of a second device, and the one or more device responses further comprise a first device response for automatically controlling the first actuator of the first device and a second device response for automatically controlling the second actuator of the second device.

In still a further embodiment, the first device response and the second device response are executed simultaneously such that the first device and the second device are simultaneously displaced during a single predetermined time period.

In yet a further embodiment, the first device response and the second device response are executed sequentially such that the first device undergoes displacement initially during a first predetermined time period, followed by displacement of the second device during a second predetermined time period.

In still a further embodiment, the first device is an instrumented treadmill, the at least one first actuator is an electric motor for rotating one or more belts of the instrumented treadmill, and the measurement assembly is a part of the instrumented treadmill; and the second device is a motion base and the at least one second actuator is a motion base actuator for displacing the motion base.

In yet a further embodiment, the at least one actuator further comprises at least one first actuator of a device and at least one second actuator of the device, and the one or more device responses further comprise a first device response for automatically controlling the first actuator of the device and a second device response for automatically controlling the second actuator of the device.

In still a further embodiment, the first device response and the second device response are executed simultaneously such that the device is simultaneously displaced by the at least one first actuator and the at least one second actuator during a single predetermined time period.

In yet a further embodiment, the first device response and the second device response are executed sequentially such that the device undergoes displacement from the at least one first actuator initially during a first predetermined time period, followed by displacement from the at least one second actuator during a second predetermined time period.

In still a further embodiment, the device is an instrumented treadmill with incline adjustment, the at least one first actuator is an electric motor for rotating one or more belts of the instrumented treadmill, the at least one second actuator is a treadmill incline actuator for adjusting an inclination angle of the instrumented treadmill, and the measurement assembly is a part of the instrumented treadmill.

In yet a further embodiment, at least one of the one or more protocols displayed in the protocol section of the graphical user interface further comprises a plurality of protocols arranged in a queue, and the at least one data processing device is further configured to execute computer executable stored instructions for: (vi) receiving an input signal from the user input device that initiates an execution of a first one of the plurality of protocols arranged in the queue; and (vii) after completing the first one of the plurality of protocols, automatically executing each successive one of the plurality of protocols arranged in the queue.

In still a further embodiment, the at least one data processing device is further configured to synchronize a capture of the output data from the at least one measurement device of the measurement assembly with the execution of the one of the one or more protocols resulting in a displacement of the surface on which the subject is disposed.

In accordance with one or more other embodiments of the present invention, there is provided a measurement and testing system that comprises a measurement assembly having a surface on which a subject is configured to be disposed, the measurement assembly including at least one measurement device that is configured to sense one or more measured quantities and output one or more signals that are representative of the one or more measured quantities; a visual display device having an output screen; a user input device, the user input device configured to enable a user of the system to input or manipulate data; and at least one data processing device operatively coupled to the at least one measurement device of the measurement assembly, the visual display device, and the user input device. The at least one data processing device including at least one hardware component, and the at least one data processing device configured to execute computer executable stored instructions, the computer executable stored instructions comprising instructions for: (i) generating a graphical user interface on the output screen of the visual display device, the graphical user interface including a protocol section, the protocol section comprising one or more protocols related to the measurement assembly; (ii) receiving an input signal from the user input device that initiates an execution of one of the one or more protocols; (iii) receiving the one or more signals that are representative of the one or more measured quantities and converting the one or more signals into output data; and (iv) displaying the output data in a portion of the graphical user interface on the output screen of the visual display device.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

Figure 3:
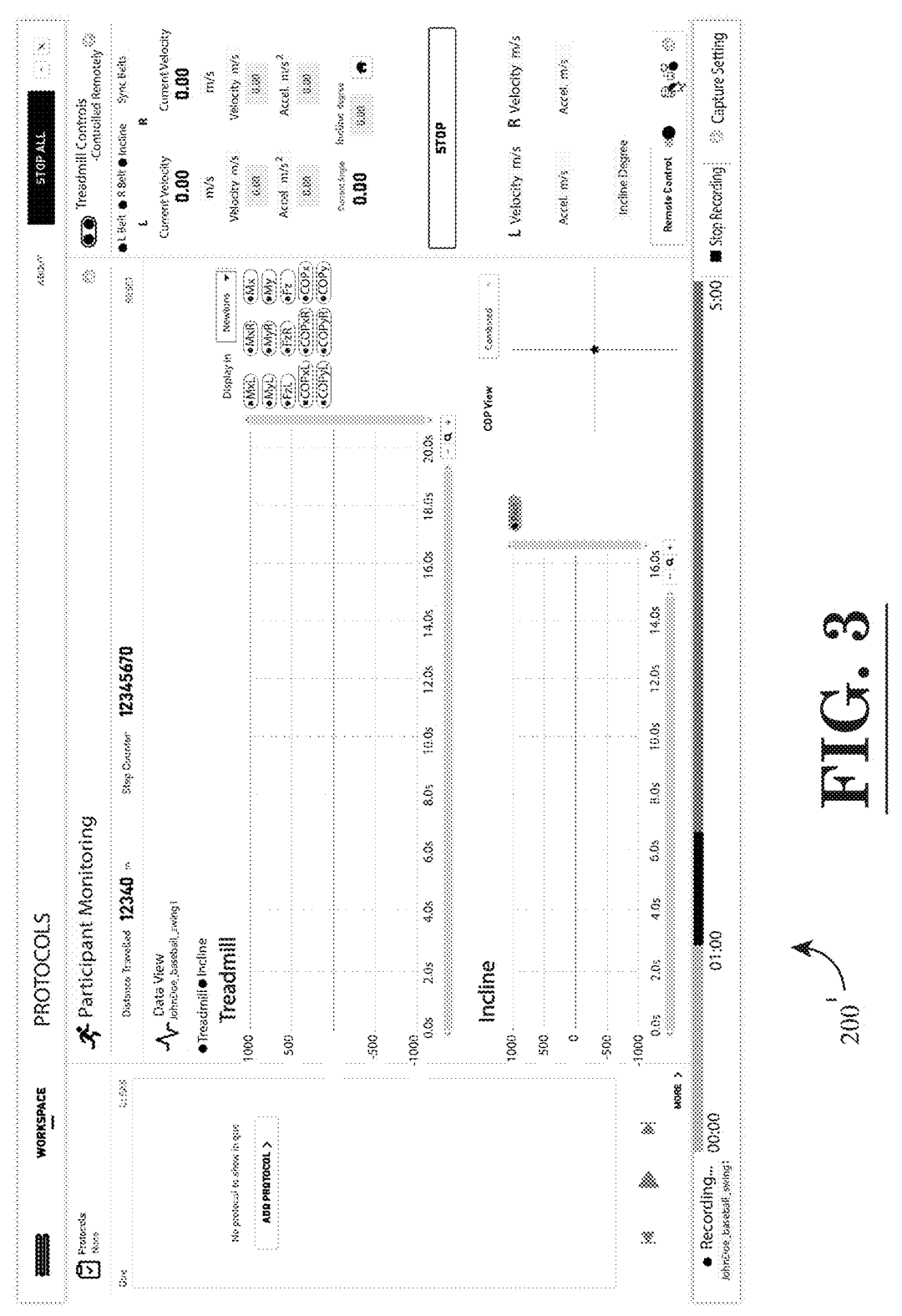

FIG. 3 is a second screenshot displayed on the user visual display device of the measurement and testing system illustrating the workspace view of the software for an incline treadmill being controlled remotely, according to an embodiment of the invention;

Throughout the figures, the same parts are always denoted using the same reference characters so that, as a general rule, they will only be described once.

DETAILED DESCRIPTION OF EMBODIMENTS OF THE INVENTION

The present invention is described herein, in an exemplary manner, with reference to hardware components, computer system architecture, and screenshots that illustrate exemplary processes carried out by the computer system. In a preferred embodiment, functional aspects of the system can be implemented by computer system instructions. These computer program instructions may be loaded directly onto an internal data storage device of a computing device (e.g., a hard drive of a computer). Alternatively, these computer program instructions could be stored on a portable computer-readable medium (e.g., a flash drive, a floppy disk, a compact disk, etc.), and then subsequently loaded onto a computing device such that the instructions can be executed thereby. In other embodiments, these computer program instructions could be embodied in the hardware of the computing device, rather than in the software thereof. It is also possible for the computer program instructions to be embodied in a combination of both the hardware and the software. Also, in the disclosure, when a reference is made to a computing device that is "configured to", "arranged to" and/or "configured and arranged to" perform a specific function (e.g., a data processing device configured and arranged to perform a specific function), it is to be understood that, in one or more embodiments of the invention, this means that the computing device is specially programmed to carry out the particular function (e.g., the data processing device being specially programmed to perform a specific function).

This description describes in general form the computer program(s) required to carry out the various features of the invention. Any competent programmer in the field of information technology could develop a functioning system using the description set forth herein.

For the sake of brevity, conventional computer system components, conventional data networking, and conventional software coding will not be described in detail herein. Also, it is to be understood that the connecting lines shown in the block diagram(s) included herein are intended to represent functional relationships and/or operational couplings between the various components. In addition to that which is explicitly depicted, it is to be understood that many alternative or additional functional relationships and/or physical connections may be incorporated in a practical application of the system.

Figure 1:
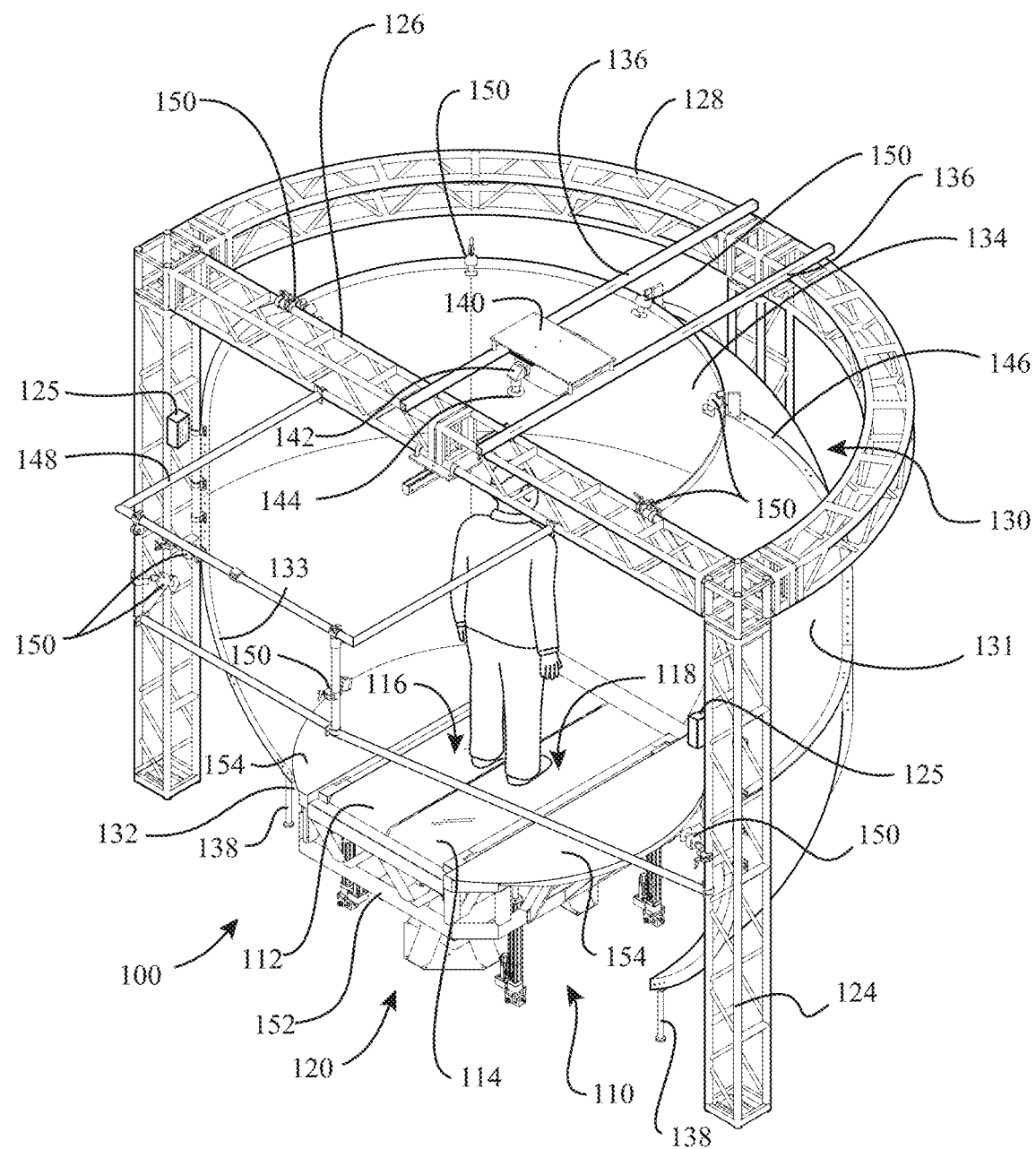
FIG. 1 is a perspective view of an illustrative measurement and testing system with a force measurement assembly in the form of an instrumented treadmill, according to an embodiment of the invention.

An exemplary embodiment of the measurement and testing system is seen generally at 100 in FIG. 1. In the illustrative embodiment, the measurement and testing system 100 generally comprises a measurement assembly 110 (e.g., an instrumented treadmill 110) that is operatively coupled to a data acquisition/data processing device 160 (i.e., a data acquisition and processing device or computing device that is capable of collecting, storing, and processing data), which in turn, is operatively coupled to a subject visual display device 130 and an operator visual display device 162 (see FIG. 8). As illustrated in FIG. 1, the instrumented treadmill 110 is configured to receive a subject thereon, and is capable of measuring the forces and/or moments applied to its belt surfaces 116, 118 by the subject.

With reference again to FIG. 1, it can be seen that the instrumented treadmill 110 is mounted to the top of a motion base subassembly 120. In the illustrative embodiment, the motion base subassembly 120 comprises a motion base 152 that is capable of displacing the instrumented treadmill 110 in a plurality of different directions. In the illustrated embodiment, the motion base 152 is in the form of a two (2) degree-of-freedom motion base. However, in one or more other embodiments, the motion base 152 may be a six (6) degree-of-freedom motion base that is capable of both translating and rotating the instrumented treadmill 110 in 3-dimensional space (i.e., translating and rotating the instrumented treadmill 110 in all three (3) coordinate directions). Referring again to the illustrative embodiment of FIG. 1, it can be seen that the instrumented treadmill 110 is disposed in the middle of a treadmill platform 154. The treadmill platform 154, which is disposed on both sides of the instrumented treadmill 110, makes it easier for the subject to get on and off of the instrumented treadmill 110 during testing.

In the illustrative embodiment, the instrumented treadmill 110 has a plurality of top surfaces (i.e., left and right rotating belts 112, 114) that are each configured to receive a portion of the body of the subject (e.g., the left belt 112 of the instrumented treadmill 110 is configured to receive the left leg of the subject, whereas the right belt 114 of the instrumented treadmill 110 is configured to receive the right leg of the subject). In one or more embodiments, a subject walks or runs in an upright position atop the treadmill 110 with the feet of the subject contacting the respective top surfaces 116, 118 of the treadmill belts 112, 114. The belts 112, 114 of the treadmill 110 are rotated by independent electric actuator assemblies with speed adjustment mechanisms. In the illustrated embodiment, each electric actuator assembly and associated speed adjustment mechanism comprises an electric motor with a variable speed control device operatively coupled thereto. Each electric actuator assembly and associated speed adjustment mechanism is capable of rotating its respective treadmill belt 112, 114 at a plurality of different speeds. The speed adjustment mechanisms adjust the speed at which each of their respective treadmill belts 112, 114 are rotated. The speed adjustment mechanisms of the instrumented treadmill 110 are operatively coupled to a programmable logic controller (PLC) 158 (see FIG. 8). The programmable logic controller 158 of the instrumented treadmill 110 is operatively connected to the data acquisition/data processing device 160 by an electrical cable. While they are not visible in the perspective view of FIG. 1 due to their location, the instrumented treadmill 110 includes a plurality of force transducers (e.g., four (4) pylon-type force transducers) disposed below each rotating belt 112, 114 of the treadmill 110 so that the loads being applied to the top surfaces of the belts 112, 114 can be measured. Advantageously, the separated belts 112, 114 of the instrumented treadmill 110 enable the forces and/or moments applied by the left and right legs of the subject to be independently determined. The pylon-type force transducers of the instrumented treadmill 110 are also operatively coupled to the treadmill programmable logic controller 158 by an electrical cable. In turn, the treadmill programmable logic controller 158 is operatively coupled to the data acquisition/data processing device 160 so that the force and moment output data of the pylon-type force transducers is capable of being analyzed and processed by the data acquisition/data processing device 160.

As mentioned above, in the illustrative embodiment, each of the treadmill belts 112, 114 is supported atop four (4) pylon-type force transducers (or pylon-type load cells) that are disposed underneath, and near each of the four corners (4) of the left rotating belt 112 of the treadmill 110 and each of the four corners (4) of the right rotating belt 114. Each of the eight (8) pylon-type force transducers has a plurality of strain gages adhered to the outer periphery of a cylindrically-shaped force transducer sensing element for detecting the mechanical strain of the force transducer sensing element imparted thereon by the force(s) applied to the belt surfaces 116, 118 of the instrumented treadmill 110. In the illustrative embodiment, each of the four (4) sets of pylon-type force transducers are mounted atop the motion base 152.

In an alternative embodiment, rather than using four (4) pylon-type force transducers on each treadmill belt assembly 112, 114, force transducers in the form of transducer beams could be provided under each treadmill belt assembly 112, 114. In this alternative embodiment, the left treadmill belt assembly 112 could comprise two transducer beams that are disposed underneath, and on generally opposite sides of the treadmill belt assembly 112. Similarly, in this embodiment, the right treadmill belt assembly 114 could comprise two transducer beams that are disposed underneath, and on generally opposite sides of the right treadmill belt assembly 114. Similar to the pylon-type force transducers, the force transducer beams could have a plurality of strain gages attached to one or more surfaces thereof for sensing the mechanical strain imparted on the beam by the force(s) applied to the surfaces 116, 118 of the instrumented treadmill 110.

Rather, than using four (4) force transducer pylons under each treadmill belt assembly 112, 114, or two spaced-apart force transducer beams under each treadmill belt assembly 112, 114, it is to be understood that the instrumented treadmill 110 can also utilize the force transducer technology described in U.S. Pat. No. 8,544,347, the entire disclosure of which is incorporated herein by reference.

In the illustrated embodiment, an electrical cable is used for the transmission of data between the instrumented treadmill 110 and the data acquisition/data processing device 160. A separate power cable is used to provide power to the instrumented treadmill 110 (e.g., a power cable connected directly to the electrical power system of the building in which the treadmill 110 is disposed). While a hardwired data connection is provided between the instrumented treadmill 110 and the data acquisition/data processing device 160 in the illustrative embodiment, it is to be understood that the instrumented treadmill 110 can be operatively coupled to the data acquisition/data processing device 160 using other signal transmission means, such as a wireless data transmission system.

Figure 8:
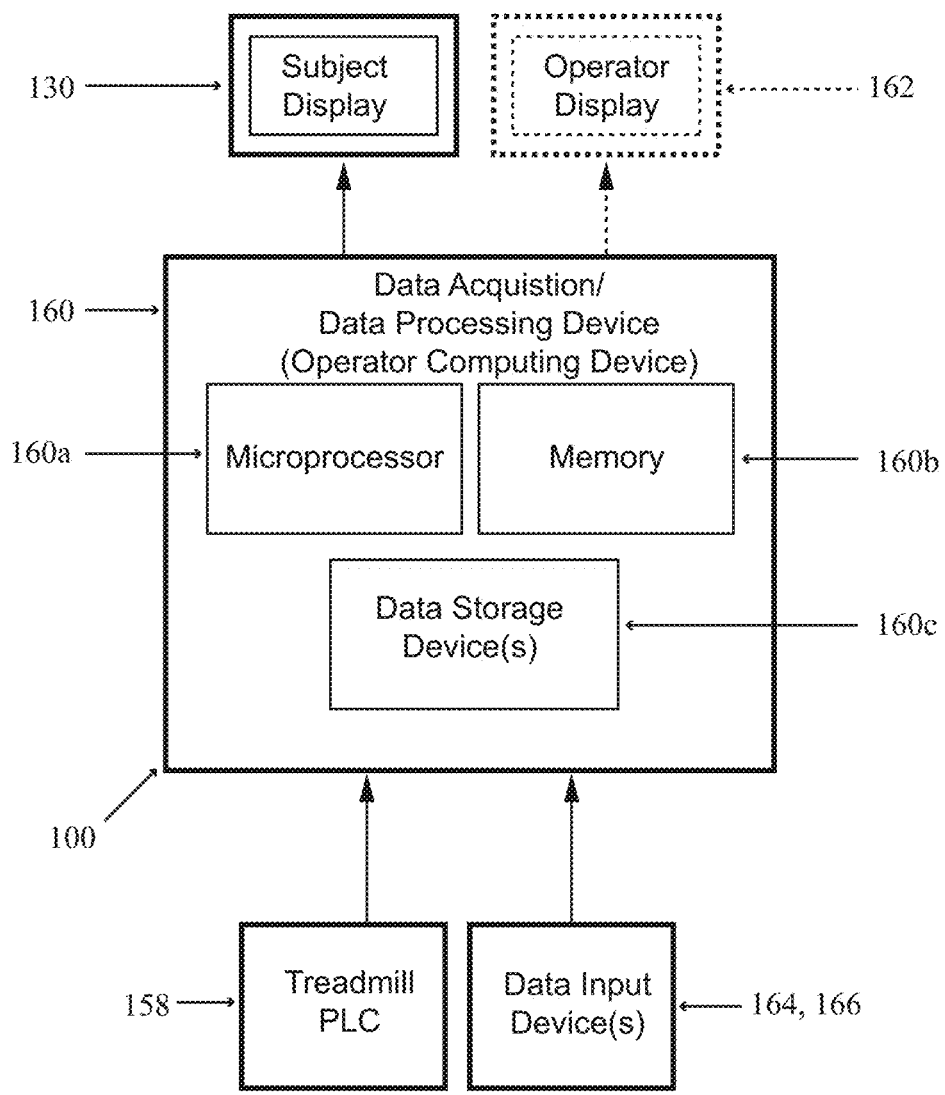
FIG. 8 is a block diagram of constituent components of the measurement and testing system, according to an embodiment of the invention.

Now, turning to FIG. 8, it can be seen that the illustrated data acquisition/data processing device 160 (i.e., the operator computing device) of the force measurement system 100 includes a microprocessor 160*a* for processing data, memory 160*b* (e.g., random access memory or RAM) for storing data during the processing thereof, and data storage device(s) 160*c*, such as one or more hard drives, compact disk drives, floppy disk drives, flash drives, or any combination thereof. As shown in FIG. 8, the programmable logic controller (PLC) 158 of the instrumented treadmill 110, and the subject visual display device 130 are operatively coupled to the data acquisition/data processing device 160 such that data is capable of being transferred between these devices 130, 158, and 160. Also, as illustrated in FIG. 8, a plurality of data input devices 164, 166, such as a keyboard and mouse, are diagrammatically shown in FIG. 8 as being operatively coupled to the data acquisition/data processing device 160 so that a user is able to enter data into the data acquisition/data processing device 160. Also, as depicted in FIG. 8, an operator visual display device 162 may also be operatively coupled to the data acquisition/data processing device 160 so that an operator (e.g., clinician) of the force measurement system 100 has a more convenient dedicated display, and thus, is not required to use the subject visual display device 130. In some embodiments, the data acquisition/data processing device 160 can be in the form of a desktop computer, while in other embodiments, the data acquisition/data processing device 160 can be embodied as a laptop computer.

Advantageously, the programmable logic controller 158 (see e.g., FIG. 8, which is a type of data processing device) provides real-time control of the treadmill actuators (i.e., motors) that control the rotation of the left and right treadmill belts 112, 114. The real-time control provided by the programmable logic controller 158 ensures that the software regulating the control of the left and right treadmill belts 112, 114 operates at the design clock rate, thereby providing fail-safe operation for subject safety. In one embodiment, the programmable logic controller 158 comprises both the treadmill control software and the input/output management software, which controls the functionality of the input/output (I/O) module of the programmable logic controller 158. In one embodiment, the programmable logic controller 158 utilizes EtherCAT protocol for enhanced speed capabilities and real-time control.

In one or more embodiments, the input/output (I/O) module of the programmable logic controller 158 allows various accessories to be added to the force measurement system 100. For example, an eye movement tracking system, such as that described by U.S. Pat. Nos. 6,113,237 and 6,152,564 could be operatively connected to the input/output (I/O) module of the programmable logic controller 158. As another example, a head movement tracking system, which is instrumented with one or more accelerometers, could be operatively connected to the input/output (I/O) module.

In one or more embodiments, an emergency stop switch may be operatively coupled to the programmable logic controller 158 in order to quasi-instantaneously stop the rotation of the treadmill belts 112, 114. As such, the emergency stop switch is a safety mechanism that protects a subject disposed on the instrumented treadmill 110 from potential injury. In an exemplary embodiment, the emergency stop switch may be in the form of a red pushbutton that can be easily pressed by a user of the force measurement system 100 in order to stop the rotation of the treadmill belts 112, 114.

Now, the acquisition and processing of the load data carried out by the force measurement system will be described. Initially, a load is applied to the instrumented treadmill 110 by a subject disposed thereon. The load is transmitted from the treadmill belt assemblies 112, 114 to its respective set of pylon-type force transducers (or force transducer beams). As described above, in the illustrated embodiment, each treadmill belt assembly 112, 114 comprises four (4) pylon-type force transducers disposed thereunder. Preferably, these pylon-type force transducers are disposed near respective corners of each treadmill belt assembly 112, 114. In a preferred embodiment, each of the pylon-type force transducers includes a plurality of strain gages wired in one or more Wheatstone bridge configurations, wherein the electrical resistance of each strain gage is altered when the associated portion of the associated pylon-type force transducer undergoes deformation resulting from the load (i.e., forces and/or moments) acting on the treadmill belt assemblies 112, 114. For each plurality of strain gages disposed on the pylon-type force transducers, the change in the electrical resistance of the strain gages brings about a consequential change in the output voltage of the Wheatstone bridge (i.e., a quantity representative of the load being applied to the measurement surface). Thus, in one embodiment, the four (4) pylon-type force transducers disposed under each treadmill belt assembly 112, 114 output a total of thirty-two (32) raw output voltages (signals) in either analog or digital form. In some embodiments, if the output voltages (signals) are in analog form, the thirty-two (32) raw output voltages (signals) from each treadmill belt assembly 112, 114 are then transmitted to a preamplifier board for preconditioning. The preamplifier board is used to increase the magnitudes of the transducer analog voltages. After which, in one or more embodiments, the analog output signals $S_{APO1}$-$S_{APO32}$ are transmitted from the analog preamplifier to the treadmill programmable logic controller (PLC) 158. In the treadmill programmable logic controller 158, the analog output signals $S_{APO1}$-$S_{APO32}$ are converted into forces, moments, centers of pressure (COP), subject center of gravity (COG), and/or sway angle for the subject. Then, the forces, moments, centers of pressure (COP), subject center of gravity (COG), and/or sway angle for the subject computed by the programmable logic controller 158 are transmitted to the data acquisition/data processing device 160 (operator computing device 160) so that they can be utilized for analyzing the movement of the subject and/or for reports displayed to an operator or clinician. Also, in yet another embodiment, the preamplifier board additionally could be used to convert the analog voltage signals into digital voltage signals (i.e., the preamplifier board could be provided with an analog-to-digital converter). In this embodiment, digital voltage signals would be transmitted to the treadmill programmable logic controller 158 rather than analog voltage signals.

In one or more embodiments, when the programmable logic controller 158 receives the voltage signals $S_{ACO1}$-$S_{ACO32}$, it initially transforms the signals into output forces and/or moments by multiplying the voltage signals $S_{ACO1}$-$S_{ACO32}$ by a calibration matrix. After which, the force and moment components (i.e., $F_{Lx}$, $F_{Ly}$, $F_{Lz}$, $M_{Ly}$, $M_{Lz}$) exerted on the left belt surface 116 of the left treadmill belt assembly 112 by the left foot of the subject, the force and moment components (i.e., $F_{Rx}$, $F_{Ry}$, $F_{Rz}$, $M_{Rx}$, $M_{Ry}$, $M_{Rz}$) exerted on the right belt surface 118 of the right treadmill belt assembly 114 by the right foot of the subject, and the center of pressure ($x_{P_L}$, $y_{P_L}$; $x_{P_R}$, $y_{P_R}$) for each foot of the subject (i.e., the x and y coordinates of the point of application of the force applied to the measurement surface by each foot) are determined by the programmable logic controller 158, and then transmitted to the data acquisition/data processing device 160.

Now, with reference again to FIG. 1, the subject visual display device 130 of the force measurement system 100 will be described in more detail. In the illustrated embodiment, the subject visual display device 130 generally comprises a projector 140 with a fisheye lens 144, and a concave projection screen 131 with a cylindrical middle portion and spherical top and bottom portions. In other words, in the illustrative embodiment, the projection screen 131 of the force measurement system 100 is not entirely spherically-shaped or dome-shaped. Advantageously, because the concave projection screen 131 is cylindrical in the middle with spherical parts on the top and bottom, a focal line is created for the subject standing on the instrumented treadmill 110, rather than a single focal point which would be created if the screen 131 were entirely spherical in shape. Thus, advantageously, individuals of different heights may be accommodated within the confines of the concave projection screen 131 without adversely affecting the focal region during the immersion (i.e., the height of a subject does not materially affect the immersive effect of the concave projection screen 131).

Turning again to the illustrative embodiment of FIG. 1, the projector 140 with the fisheye-type lens 144 projects a light beam through a semi-circular cutout 134 in the top of the concave projection screen 131. In FIG. 1, it can be seen that the fisheye lens 144 is connected to the body of the projector 140 by an elbow fitting 142. Also, as shown in FIG. 1, the concave projection screen 131 may be provided with a peripheral flange 133 therearound.

Advantageously, the concave projection screen 131 is a continuous curved surface that does not contain any lines or points resulting from the intersection of adjoining planar or curved surfaces (i.e., all section seams in the screen 131 may be filled so as to form a continuous curved surface facing the subject). Thus, the projection screen 131 is capable of creating a completely immersive visual environment for a subject being tested on the instrumented treadmill 110 because the subject is unable to focus on any particular reference point or line on the screen 131. As such, the subject becomes completely immersed in the virtual reality scene(s) being projected on the concave projection screen 131, and thus, his or her visual perception can be effectively altered during a test being performed using the force measurement system 100 (e.g., a balance test). In order to permit a subject to be substantially circumscribed by the generally hemispherical projection screen 131 on three sides, the bottom of the screen 131 is provided with a semi-circular cutout 132 in the illustrative embodiment. While the concave projection screen 131 thoroughly immerses the subject in the virtual reality scene(s), it advantageously does not totally enclose the subject. Totally enclosing the subject could cause him or her to become extremely claustrophobic. Also, the clinician would be unable to observe the subject or patient in a totally enclosed environment. As such, the illustrated embodiment of the force measurement system 100 does not utilize a totally enclosed environment, such as a closed, rotating shell, etc. Also, the subject visual display device 130 is not attached to the subject, and it is spaced apart from the instrumented treadmill 110.

In one embodiment of the invention, the generally hemispherical projection screen 131 is formed from a suitable material (e.g., an acrylic, fiberglass, fabric, aluminum, etc.) having a matte gray color. A matte gray color is preferable to a white color because it minimizes the unwanted reflections that can result from the use of a projection screen having a concave shape. Also, in an exemplary embodiment, the projection screen 131 has a diameter (i.e., width $W_S$) of approximately 180 inches and a depth $D_S$ of approximately 90 inches. Although, those of ordinary skill in the art will readily appreciate that other suitable dimensions may be utilized for the projection screen 131, provided that the selected dimensions for the screen 131 are capable of creating an immersive environment for a subject disposed on the instrumented treadmill 110 (i.e., the screen 131 of the subject visual display device 130 engages enough of the subject's peripheral vision such that the subject becomes, and remains immersed in the virtual reality scenario). In one or more embodiments, the projection screen 131 fully encompasses the peripheral vision of the subject (e.g., by the coronal plane of the subject being disposed inwardly from the flange 133 within the confines of the screen 131). In other words, the output screen 131 of the at least one visual display 130 at least partially circumscribes three sides of a subject. The overhanging top portion of the projection screen 131 creates an efficient manner in which to fully immerse the subject. If the projection screen 131 were not formed with the overhanging top portion, the height of the projection screen 131 would have to be greatly increased in order to create the same full immersive effect. As such, the use of the concave projection screen 131 with the spherical, overhanging top portion allows the screen 131 to be much shorter, while still achieving the desired effect of the total immersion of the subject. In the illustrated embodiment, the concave projection screen 131 of the at least one visual display 130 is formed from a plurality of sections. As shown in FIG. 1, each of these screen sections comprises one or more connector flanges 146 that are used to connect the screen sections to one another (e.g., the screen sections are bolted to one another at the connector flanges 146).

In a preferred embodiment, the data acquisition/data processing device 160 is configured to convert a two-dimensional (2-D) image, which is configured for display on a conventional two-dimensional screen, into a three-dimensional (3-D) image that is capable of being displayed on the hemispherical output screen 131 without excessive distortion. That is, the data acquisition/data processing device 160 executes a software program that utilizes a projection mapping algorithm to "warp" a flat 2-D rendered projection screen image into a distorted 3-D projection image that approximately matches the curvature of the final projection surface (i.e., the curvature of the hemispherical output screen 131), which takes into account the distortion of the lens 144 of the projector 140. In particular, the projection mapping algorithm utilizes a plurality of virtual cameras and projection surfaces (which are modeled based upon the actual projection surfaces) in order to transform the two-dimensional (2-D) images into the requisite three-dimensional (3-D) images. Thus, the projector lens 144 information and the concave projection screen 131 dimensional data are entered as inputs into the projection mapping algorithm software. When a human subject is properly positioned in the confines of the hemispherical output screen 131, he or she will see a representation of the virtual reality scene wrapping around them instead of only seeing a small viewing window in front of him or her. Advantageously, using a software package comprising a projection mapping algorithm enables the system 100 to use previously created 3-D modeled virtual worlds and objects without directly modifying them. Rather, the projection mapping algorithm employed by the software package merely changes the manner in which these 3-D modeled virtual worlds and objects are projected into the subject's viewing area.

As described above, with reference to FIG. 1, it can be seen that the fisheye lens 144 of the projector 140 is connected to the body of the projector 140 by an elbow fitting 142. In other words, the fisheye lens 144 is disposed at a non-zero, angled orientation relative to a body of the projector 140. In the illustrated embodiment, the non-zero, angled orientation at which the fisheye lens 144 is disposed relative to the body of the projector 140 is approximately 90 degrees. The elbow fitting 142 comprises a one-way mirror disposed therein for changing the direction of the light beam emanating from the projector 140. As illustrated in FIG. 1, the fisheye lens 144 is disposed at approximately the apex of the concave projection screen 131, and it extends down through the cutout 134 at the top of the screen 131.

Those of ordinary skill in the art will also appreciate that the subject visual display device 131 may utilize other suitable projection means. For example, rather using an overhead-type projector 140 as illustrated in FIG. 1, a direct or rear projection system can be utilized for projecting the image onto the screen 131, provided that the direct projection system does not interfere with the subject's visibility of the target image. In another alternative embodiment, two projectors, each having a respective fisheye-type lens, are used to project an image onto the screen 131. In this alternative embodiment, the two projectors with respective fisheye-type lens project intersecting light beams through the cutout 134 in the top of the generally hemispherical projection screen 131. Advantageously, the use of two projectors with respective fisheye-type lens, rather than just a single projector 140 with a fisheye lens 144, has the added benefit of removing shadows that are cast on the output screen 131 by the subject disposed on the instrumented treadmill 110.

Turning again to FIG. 1, it can be seen that, in the illustrative embodiment, the concave projection screen 131 may be supported from a floor surface using a screen support structure formed using a plurality of truss members 124, 126, 128. As shown in FIG. 1, the screen support structure 124, 126, 128 is used to elevate the projection screen 131 a predetermined distance above the floor of a room. With continued reference to FIG. 1, it can be seen that the illustrated screen support structure comprises a plurality of generally vertical truss members 124 (i.e., three (3) generally vertical truss members 124) that support a plurality of generally horizontal truss members 126, 128 (i.e., two (2) generally horizontal truss members 126, 128), which are disposed at the top of the projection screen 131. As shown in FIG. 1 of the illustrated embodiment, the plurality of generally horizontal truss members 126, 128 include a first linear truss member 126 disposed in the front of the projection screen 131, and a second semi-circular truss member 128 disposed around the curved back side of the projection screen 131. In particular, the two (2) front vertical truss members 124 are securely attached to the peripheral flange 133 of the concave projection screen 131 (e.g., by using a plurality of fasteners and brackets on each side of the flange 133). Because the screen support structure 124, 126, 128 is mostly attached to the upper portion (e.g., upper half) of the screen 131, the screen 131 is generally supported above its center-of-gravity, which advantageously results in a screen mounting arrangement with high structural stability. As shown in FIG. 1, one of the plurality of lower leg members 138 are disposed on each of the opposed lateral sides of the screen 131. Also, each of the lower leg members 138 may be provided with a height-adjustable foot for adjusting the height of the screen 131 relative to the floor. Also, as shown in FIG. 1, the projector 140 is supported above the screen 131 by a pair of spaced-apart projector support rails 136, each of which is secured directly to the first linear truss member 126 and the second semi-circular truss member 128 of the screen support structure 124, 126, 128, and not directly to the screen 131, so as to minimize the transmission of vibrations from the projector 140 to the hemispherical projection screen 131. Advantageously, the mounting arrangement of the projector 140 on the spaced-apart projector support rails 136 affords adjustability of the projector 140 in a front-to-back direction. It is highly desirable for the hemispherical projection screen 131 to be maintained in a stationary position essentially free from external vibrations so that the subject is completely immersed in the virtual environment being created within the hemispherical projection screen 131. Advantageously, the structural rigidity afforded by the screen support structure 124, 126, 128 of FIG. 1 virtually eliminates the transmission of vibrations to the projection screen 131, including those vibrations emanating from the building itself in which the force measurement system 100 is located. In particular, the screen support structure 124, 126, 128 is designed to minimize any low frequency vibrations that are transmitted to the screen 131.

In the illustrative embodiment, as shown in FIG. 1, the top surfaces 116, 118 of the treadmill belts 112, 114 are horizontally spaced apart from the screen support structure 124, 126, 128. In other words, there is a gap horizontally separating the instrumented treadmill 110 from the hemispherical projection screen 131 and its associated screen support structure 124, 126, 128.

As shown in the illustrative embodiment of FIG. 1, the force measurement system 100 may be additionally provided with a motion capture system comprising a plurality of cameras 150. Referring to FIG. 1, it can be seen that a plurality of cameras 150 are disposed around the instrumented treadmill 110 so that the cameras 150 at least partially surround the subject disposed on the treadmill 110. In the illustrative embodiment, the cameras 150 are used to track positions of a plurality of markers disposed on a subject as the subject moves his or her torso and limbs in 3-dimensional space. The markers on the subject are used to record the position of the torso and limbs of the subject in 3-dimensional space.

In the illustrative embodiment, with reference to FIG. 1, it can be seen that a first plurality of cameras 150 are circumferentially spaced apart around the top cutout 134 in the concave projection screen 131 (i.e., the first plurality of cameras 150 are structurally attached in a load bearing manner around the top cutout 134 of the concave projection screen 131). For example, in the illustrative embodiment, the cameras 150 may be generally equally spaced apart about the circumference of the top screen cutout 134. While five (5) cameras 150 are depicted around the circumference of the top screen cutout 134 in the illustrative embodiment, one of ordinary skill in the art will appreciate that more or less cameras may be utilized, provided that the motion of the subject is capable of being captured from substantially all angles. Turning again to FIG. 1, it can be seen that a second plurality of cameras 150 are spaced apart in front of the instrumented treadmill 110 (i.e., on the open front side of the projection screen 131). In particular, as shown in the illustrative embodiment of FIG. 1, one (1) camera 150 is disposed on each of the generally vertical truss members 124 near the approximate middle of the truss member 124 (i.e., each camera 150 is structurally attached to a respective vertical truss members 124 in a load bearing manner approximately mid-height on the truss member 124). Two (2) additional cameras 150 are attached to the camera mounting structure 148 that extends outwardly from the truss members 124, 126 (i.e., the two additional cameras 150 are structurally attached to the camera mounting structure 148 in a load bearing manner). With combined reference to FIG. 1, it can be seen that the camera mounting structure 148 is attached to each of the vertical truss members 124 and the generally linear truss member 126. The camera mounting structure 148 enables the two (2) additional front cameras 150 to be spaced significantly in front of the cameras 150 that are mounted to the respective vertical truss members 124 so that the movements of the subject may be better captured by the motion capture system. While a total of nine (9) cameras 150 are depicted in the illustrative embodiment of FIG. 1, one of ordinary skill in the art will appreciate that more or less cameras can be utilized, provided that the motion of the subject is capable of being captured from substantially all angles.

In the illustrative embodiment, the cameras 150 depicted in FIG. 1 may be in the form of infrared-type (IR) or near infrared-type (NIR) cameras having an angular field of view range between approximately 40 degrees and approximately 80 degrees (or between 40 degrees and 80 degrees). More particularly, in one or more embodiments, the angular field of view range of the cameras 150 may be between approximately 50 degrees and approximately 70 degrees (or between 50 degrees and 70 degrees). Also, in one or more exemplary embodiments, the cameras 150 depicted in FIG. 1 may have a resolution of approximately 1.0 Megapixels, a maximum frame rate of approximately 250 feet per second (fps), and a 4 millimeter to 12 millimeter (4-12 mm) zoom lens. The cameras 150 are positioned in the force measurement system 100 of FIG. 1 so that each marker disposed on a subject standing on the instrumented treadmill 110 is captured by at least two (2) of the cameras 150, and preferably, three (3) of the cameras 150.

In one embodiment of the invention, a subject has a plurality of single reflective markers applied to anatomical landmarks (e.g., the iliac spines of the pelvis, the malleoli of the ankle, and the condyles of the knee), and/or clusters of markers applied to the middle of body segments. As the subject executes particular movements on the instrumented treadmill 110, the data acquisition/data processing device 160 is specially programmed to calculate the trajectory of each reflective marker in three (3) dimensions using the position of the marker captured by the cameras 150. Then, once the positional data is obtained using the motion capture system of FIG. 1, inverse kinematics may be employed in order to further determine the joint angles of the subject. That is, the motion capture system of FIG. 1 generates motion capture data that is representative of the captured motion of the body portions of the subject, and the data acquisition/data processing device 160 is specially programmed to determine the position of the body of the subject (i.e., limbs, torso, head, etc.) and the joint angles of the subject from the motion capture data generated by the motion capture system.

Moreover, in the illustrative embodiment, the motion capture system may also be used to determine the forces and/or moments acting on the joints of a subject. An exemplary calculation procedure for the joint angles, velocities, and accelerations will be described hereinafter. Initially, the plurality of cameras 150 are calibrated using the image coordinates of calibration markers and the three-dimensional (3-D) relationship of calibration points such that a plurality of calibration parameters are generated. In the illustrative embodiment, the calibration of the plurality of cameras 150 is performed using a Direct Linear Transformation ("DLT") technique and yields eleven (11) DLT parameters. However, it is to be understood that, in other embodiments of the invention, a different technique can be used to calibrate the plurality of cameras 150. Then, the perspective projection of the image coordinates of the body markers is performed using the calibration parameters so that the image coordinates are transformed into actual three-dimensional (3-D) coordinates of the body markers. Because the digitization of the marker images involves a certain amount of random error, a digital filter is preferably applied to the three-dimensional (3-D) coordinates of the markers to remove the inherent noise. Although, it is to be understood that the use of a digital filter is optional, and thus is omitted in some embodiments of the invention. In the illustrative embodiment, local coordinate systems are utilized to determine the orientation of the body segments relative to each other. After which, rotational parameters (e.g., angles, axes, matrices, etc.) and an inverse kinematics model are used to determine the joint angles. The inverse kinematics model contains the details of how the angles are defined, such as the underlying assumptions that are made regarding the movement of the segments relative to each other. For example, in the inverse kinematics model, the hip joint could be modeled as three separate revolute joints acting in the frontal, horizontal, and sagittal plane, respectively. Then, in the illustrative embodiment, differentiation is used to determine the joint velocities and accelerations from the joint angles. Although, one of ordinary skill in the art will appreciate that, in other embodiments of the invention, both differentiation and analytical curve fitting could be used to determine the joint velocities and accelerations from the joint angles.

Next, the manner in which the joint forces and moments are calculated in the illustrative embodiment will be explained. Initially, anthropometric data is applied to a segment model in order to determine the segment inertial parameters. Then, by using the segment inertial parameters together with the joint velocities and accelerations and the force plate measurements, joint and body segment kinetics are used to determine the desired joint forces and moments. In the illustrative embodiment, Newton-Euler Formulations are used to compute the joint forces and moments. However, it is to be understood that the invention is not so limited. Rather, in other embodiments of the invention, the kinetics analysis could be carried out using a different series of equations. An exemplary determination of the joint reaction forces and joint moments acting on the ankle of the subject is described in detail in U.S. Pat. No. 8,847,989 (e.g., refer to FIGS. 35 and 36 and equations (4)-(7)). The entire disclosure of U.S. Pat. No. 8,847,989 is incorporated herein by reference.

While the motion capture system of FIG. 1 described above employs a plurality of reflective markers, it is to be understood that the invention is not so limited. Rather, in another embodiment of the invention, a markerless motion detection/motion capture system is utilized. The markerless motion capture system uses a plurality of high speed video cameras to record the motion of a subject without requiring any markers to be placed on the subject. Also, while the illustrative embodiment utilizes a plurality of infrared-type (IR) or near infrared-type (NIR) cameras 150, it is to be understood that a non-infrared, optical-based motion detection/motion capture system may alternatively be used. For example, in one alternative embodiment, the optical motion capture system utilizes visible light, rather than infrared light. In addition, an alternative motion capture system may utilize an infrared (IR) emitter to project a plurality of dots onto objects in a particular space as part of a markerless motion capture system. For example, in these one or more alternative embodiments, the markerless motion capture system may comprise a motion capture device with one or more cameras, one or more infrared (IR) depth sensors, and one or more microphones, which may be used to provide full-body three-dimensional (3D) motion capture, facial recognition, and voice recognition capabilities. It is also to be understood that, rather than using an optical motion detection/capture system, a suitable magnetic or electro-mechanical motion detection/capture system may also be employed to determine the position and joint angles of the subject on the instrumented treadmill 110.

In the illustrative embodiment, with reference again to FIG. 1, it can be seen that speakers 125 may be provided on the vertical truss members 124. The speakers 125 are operatively coupled to the data acquisition/data processing device 160 so as to be capable of providing audio output for various purposes, such as for providing auditory feedback to the subject regarding his or her movements on the instrumented treadmill 110.

Now, specific user application functionality of the exemplary measurement and testing system 100 will be described in detail. It is to be understood that the aforedescribed functionality of the measurement and testing system 100 can be carried out by the data processing device 160 (i.e., the local computing device) utilizing software, hardware, or a combination of both hardware and software. For example, the data acquisition/data processing device 160 can be specially programmed to carry out the functionality described hereinafter. In one embodiment of the invention, the computer program instructions necessary to carry out this functionality may be loaded directly onto an internal data storage device 160c of the data acquisition/data processing device 160 (e.g., on a hard drive thereof) and subsequently executed by the microprocessor 160a of the data acquisition/data processing device 160. Alternatively, these computer program instructions could be stored on a portable computer-readable medium (e.g., a flash drive, a floppy disk, a compact disk, etc.), and then subsequently loaded onto the data acquisition/data processing device 160 such that the instructions can be executed thereby. In one embodiment, these computer program instructions are embodied in the form of a measurement and testing software program executed by the data acquisition/data processing device 160. In other embodiments, these computer program instructions could be embodied in the hardware of the data acquisition/data processing device 160, rather than in the software thereof. It is also possible for the computer program instructions to be embodied in a combination of both the hardware and the software. In other embodiments, the computer program instructions could be stored on and executed by a cloud server that is operatively coupled to the data acquisition/data processing device 160.

Figure 2:
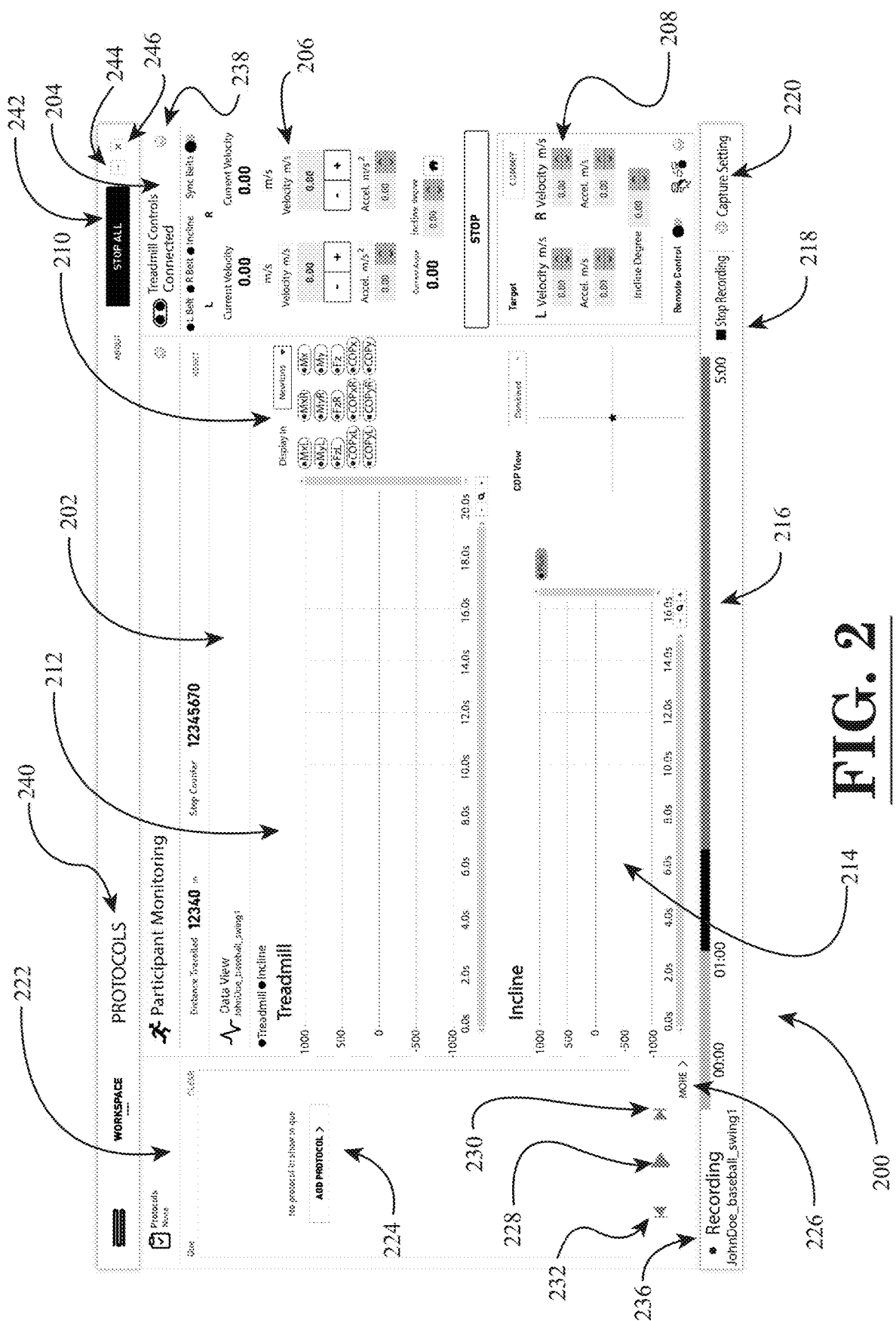
FIG. 2 is a first screenshot displayed on a user visual display device of a measurement and testing system illustrating the workspace view of the software for an incline treadmill, according to an embodiment of the invention.
Figure 4:
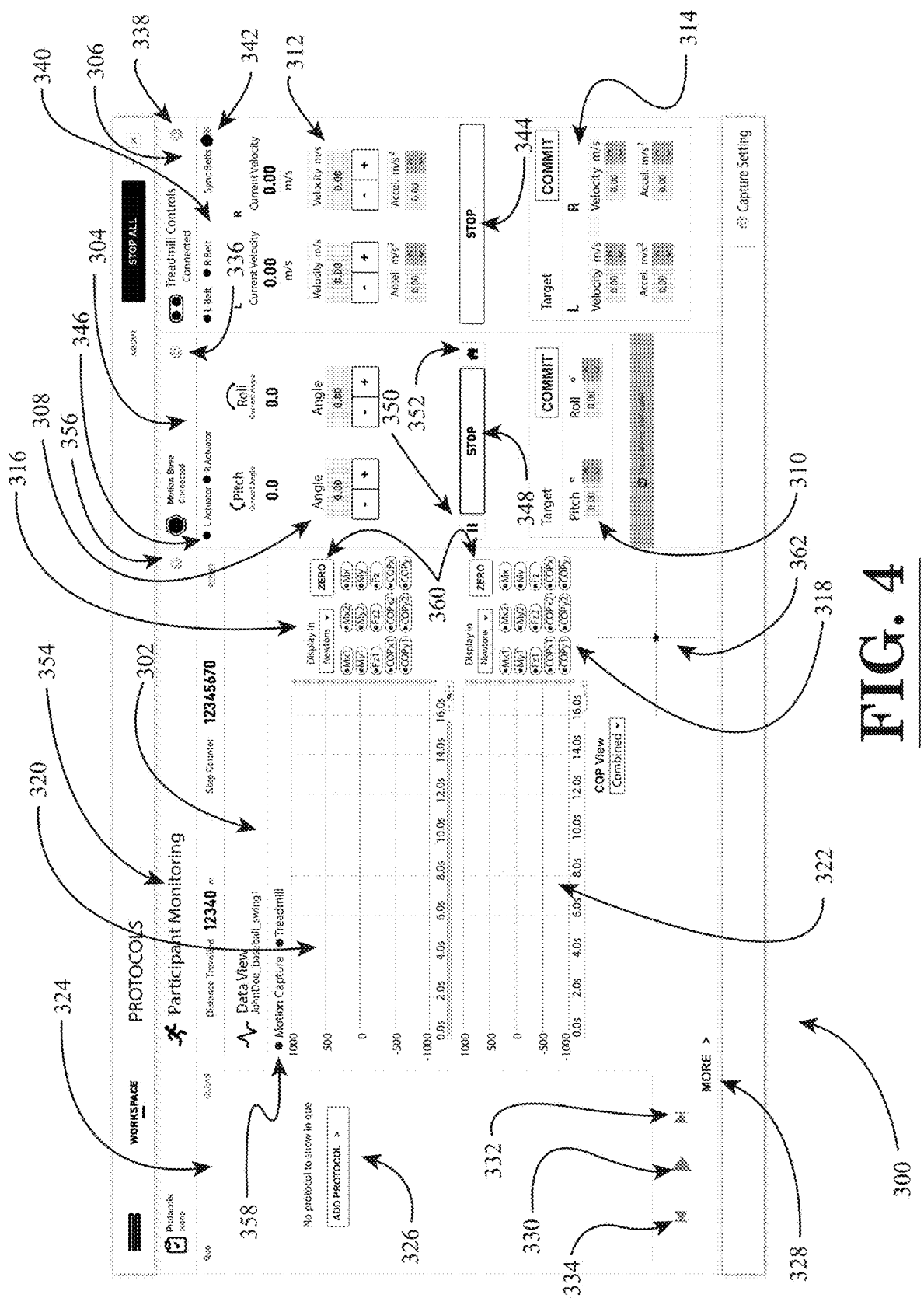
FIG. 4 is a third screenshot displayed on the user visual display device of the measurement and testing system illustrating the workspace view of the software for a motion base and treadmill, according to an embodiment of the invention.

According to one aspect of the illustrative embodiment, referring initially to FIG. 2, the data processing device 160 of the measurement and testing system 100 is configured and arranged to generate a workspace view graphical user interface 200 that includes data view portion 202 and a treadmill control portion 204. In the illustrative embodiment, the workspace view is one of the main windows of the software. This "tab" of the software comprises the treadmill control portion 204 (i.e., treadmill control "card" 204) on the right side of the screen. Cards are the terms used herein for the vertical panels within the workspace. FIG. 2 shows an example of a workspace view for an inclined treadmill, which includes a single control card 204. FIG. 4 shows an example of a user interface configuration 300 for a system with a treadmill and a motion base. In FIG. 4, the workspace view graphical user interface 300 includes a data view portion 302, a motion base control portion 304, and a treadmill control portion 306. As such, in FIG. 4, there are two (2) control cards 304, 306 on the screen, one for the motion base and another for the treadmill. These control cards 304, 306 include all the controls to operate their respective devices with both quick controls and target/commit controls. Quick controls are controls that respond immediately upon pressing the increment/decrement buttons for parameters, such as treadmill speed or incline angle (e.g., see section 206 of control card 204 in FIG. 2, and sections 308, 312 of control cards 304, 306 in FIG. 4). Target/commit controls are used for setting a specific value as an input, and the system will respond only when the user presses the "commit" button (e.g., see section 208 of control card 204 in FIG. 2, and sections 310, 314 of control cards 304, 306 in FIG. 4). For example, if the treadmill is stopped, and the user wants to go directly to a 3 m/s speed, the user could enter '3' and then press "commit", and the treadmill would go directly to 3 m/s at an acceleration that is specified.

In the illustrative embodiment, with reference again to FIGS. 2 and 4, it can be seen that the data view card 202, 302 is provided in the center of the screen. The data view card 202, 302 contains the real-time data stream of all the data within the system. In illustrative embodiment, as shown in FIGS. 2 and 4, the data view card 202, 302 may include treadmill velocity for each belt, all force and moment data for each belt, center of pressure data, incline angle for incline base (if included), and pitch and roll data for motion base (if included). These various data streams can be toggled in the graph using the colored toggle buttons 210, 316, 318 to the right of the graphs 212, 214, 320, 322.

In addition, as shown in the illustrative embodiment of FIG. 2, the workspace view graphical user interface 200 may further include a data capture bar 216 along the bottom of the screen. In the illustrative embodiment, the data capture bar 216 depicts the progress of a user's data capture using a green bar that moves across the bottom of the screen. In the bottom right corner of the illustrative workspace view graphical user interface 200, there is further provided capture settings and stop/start capture buttons 218, 220. The features of the data capture bottom screen portion all function together to save and export the data to a comma separated values (CSV) file.

In the illustrative embodiment, referring again to FIGS. 2 and 4, the protocol builder card 222, 324 is on the left side of the screen. The protocol builder is explained further below, but this section of the screen is where any currently running protocols are listed if the user is using that feature.

Figure 5:
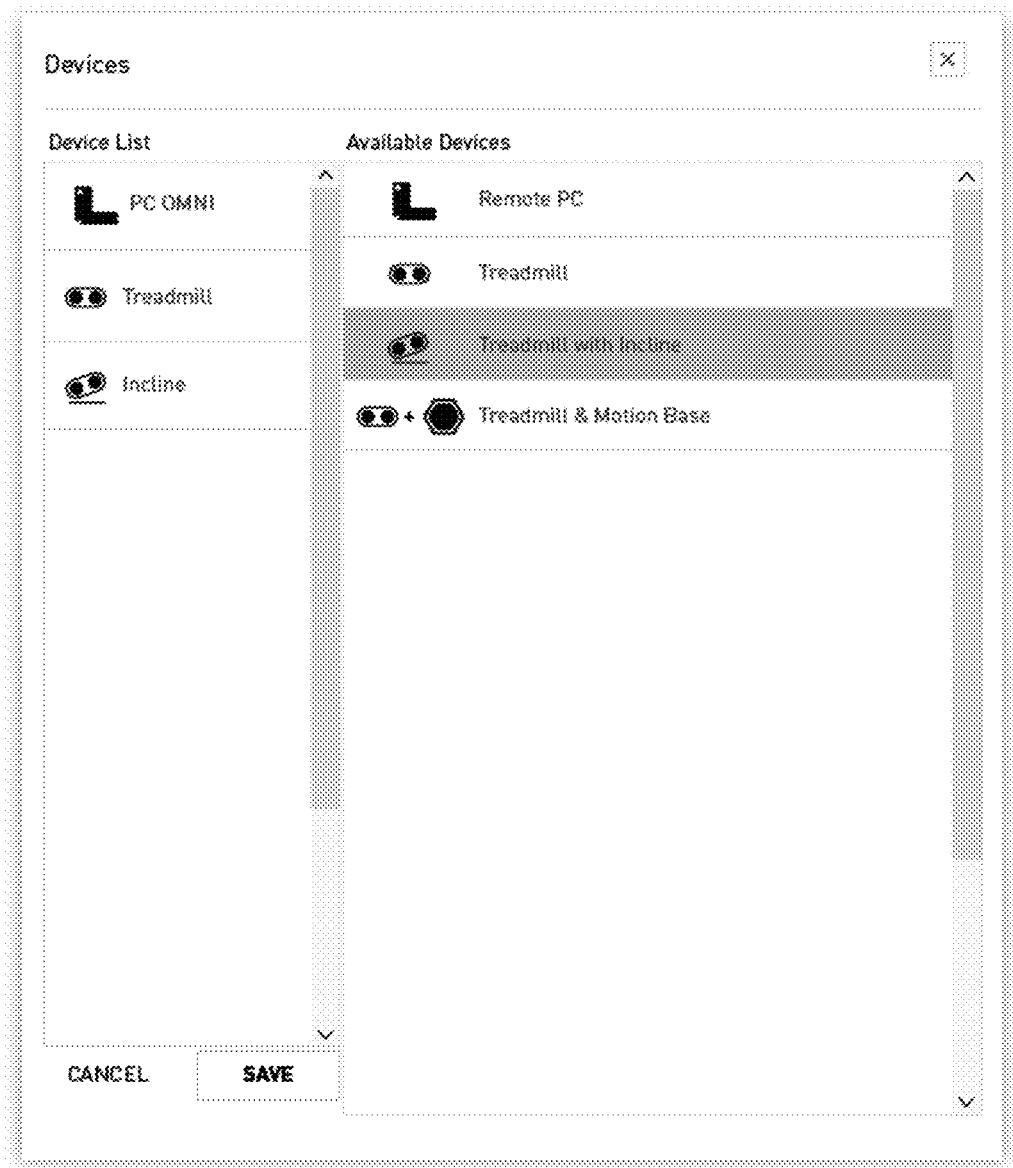
FIG. 5 is a fourth screenshot displayed on the user visual display device of the measurement and testing system illustrating the device selection window of the software, according to an embodiment of the invention.
Figure 6:
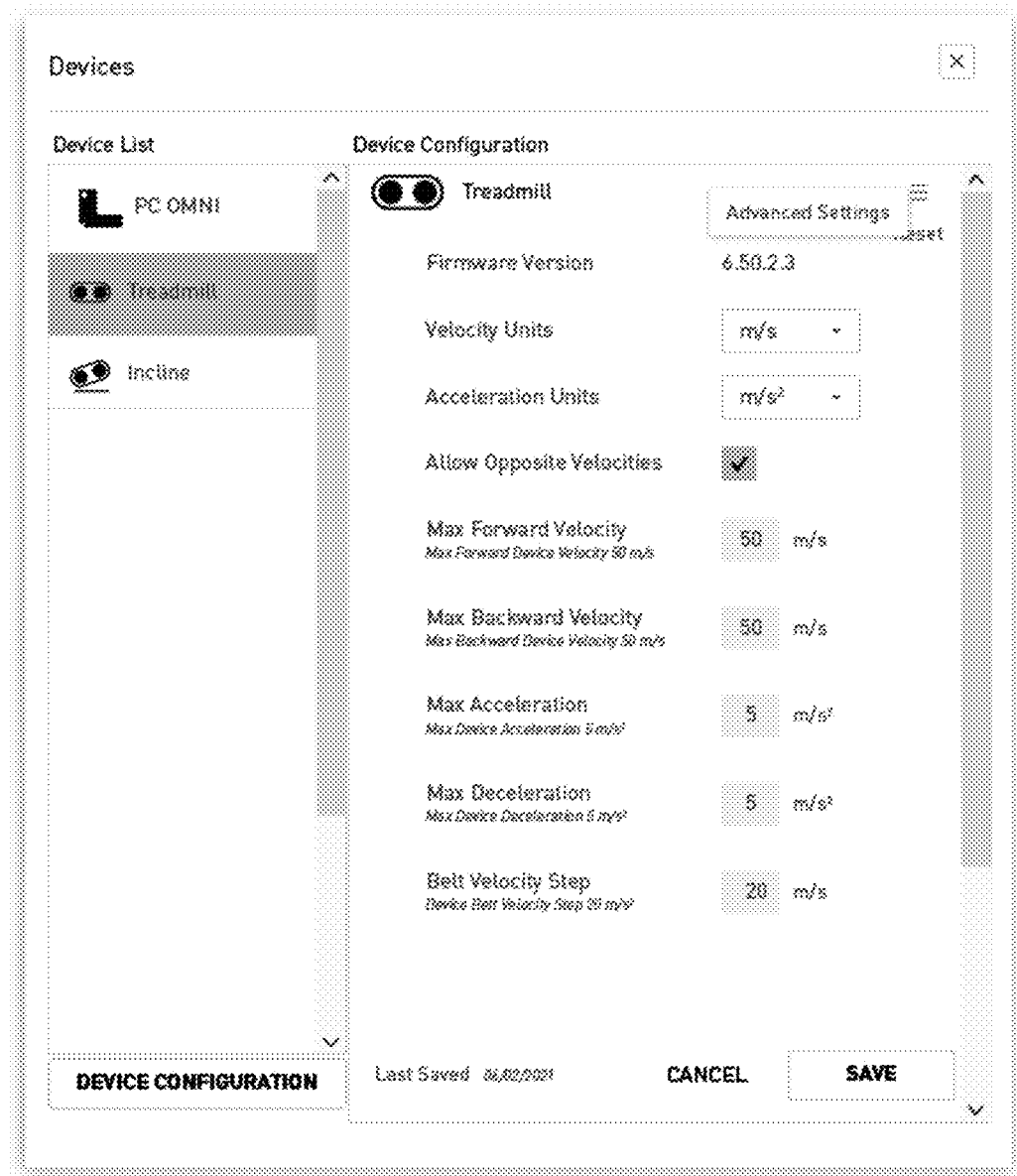
FIG. 6 is a fifth screenshot displayed on the user visual display device of the measurement and testing system illustrating the device configuration window of the software, according to an embodiment of the invention.

Next, with reference to FIG. 5, in the illustrative embodiment, the data processing device 160 of the measurement and testing system 100 is configured and arranged to generate a device selection menu 400 that enables a user to select the hardware devices that are available, in order to allow the user to set up his or her software user interface. FIG. 5 illustrates an exemplary screenshot 400 of the device selection window. The purpose of this feature is to hide any unnecessary elements throughout the software if the user does not own the required hardware. For example, if the user only has a base model treadmill with no additional accessories (e.g., incline or motion base), then the user would not see any controls, data, or user interface elements related to hardware that he or she has not configured (i.e., no motion base control card or data view if the user does not have a motion base). The device selection menu also houses all the settings and advanced settings for the devices once the user has configured those devices, as shown in the screenshot 500 of FIG. 6.

With reference again to FIG. 2, in the illustrative embodiment, the top bar 240 of the software user interface will be described. As shown in FIG. 2, the top bar 240 generally includes a "Workspace" button and a "Protocol" button. The workspace button on the top bar 240 opens the main workspace page 200 of the software. From here, users can manage most of their work according to the connected devices. This page contains many sections that can be used daily from monitoring the participant, viewing the data of the devices to controlling the devices (the Workspace will be described in detail hereinafter). The protocol button on the top bar 240 opens the protocols page. From here, users can control and edit the protocols. The protocol page allows users to create new protocols, edit existing ones or create playlists with their protocols in an order of their choice and so much more (the Protocols will be described in detail hereinafter). The "About" button on the top bar 240 opens the About window that gives the user information about the software version and the connected devices. The "X" button at the right corner on the top bar 240 will close the About window.

In one or more embodiments, the top bar 240 may further include a "Devices" button that opens the "Devices" window (refer to FIG. 5). From here, users can set up their devices and can obtain information about the software version and the connected devices. The "X" button at the corner will close the "Devices" window (see FIG. 5). The "Devices" window includes a Device List, which is the list view where users are able to see which devices are connected, and use it as a navigation to see information about them. When the software first starts up, the device list should be empty. The "Devices" window may further include a "Configure Devices" button. To set up devices, preferably a technician from the device manufacturer clicks this button. When clicked, a warning message appears, notifying the users not to click it unless they have consulted with a technician from the device manufacturer. In the warning message window, the "Cancel" button will close the window. The "OK" button will close the window and display the Available Devices section on the "Devices" window. The "X" button will close the window. When the "OK" button is selected by a user, there will be a list of supported devices visible on the Available Devices section on the "Devices" window.

In the illustrative embodiment, when any of the devices on the right is selected in the "Devices" window (see FIG. 5), they will be added to the device list. For example, when the "Remote PC" is clicked by a user, the software will add a Remote PC device to the Device List. When the "Treadmill" is clicked by a user, the software will add a Treadmill device to the Device List. When the "Treadmill with Incline" is clicked by a user, the software will add a Treadmill device and an Incline device to the Device List. If there is already a Treadmill on the list, then it will just add the Incline. When the "Treadmill & Motion Base" is clicked by a user, the software will add a Treadmill device and a Motion Base device to the Device List. If there is already a Treadmill on the list, then it will just add the Motion Base. Additional information on the settings of those devices is explained in conjunction with the specific device settings below. A "X" button may be located at the end of each device on the Device List, which is clicked by a user to remove the added device. In the "Devices" window, the "Cancel" button will reverse all the changes that have been made and close the Available Devices section. In the "Devices" window, the "Save" button will save all the changes that have been made and close the Available Devices section. When the set-up of the devices is finished, all the software will change accordingly. There will be only the selected devices controls and the data visible on the workspace and on the protocol builder.

In the illustrative embodiment, turning again to FIG. 2, the top bar 240 of the software user interface further includes a Stop All" button 242 and "–" and "x" buttons 244, 246. The "Stop All" button 242 acts as an emergency stop and when pressed will stop the connected devices from moving in a safe manner. If a protocol is playing, the protocol will stop and if the motion base, treadmill, and/or incline are moving, they will stop moving at an appropriate velocity. The "–" button 244 minimizes the software user interface, while the "x" button 246 closes the software interface. When the "x" button 246 is pressed, a notification window will appear to confirm if the user is sure about exiting the software, which also means all the devices will stop their movement. In the notification window, if the user presses the "No" button, the notification window will close and the software will operate as before. In the notification window, if the user presses the "Yes" button, all devices will be stopped, and the software will close down. The "X" button on the notification window will act in the same manner as the "No" button, and just close the notification window.

Now, with reference to FIG. 4, the details of the workspace view graphical user interface 300 will be described. In the illustrative embodiment, the workspace page may be the controller for the treadmill and motion base system. From this dashboard, a user can run the protocols and control the devices, such as the treadmill. This page allows the user to control instrumented treadmill and the motion base independently (see FIG. 4), plus the incline, if connected. The workspace page is where the user goes to quickly begin using the system. From this view, the user can run the treadmill and motion base independently (and incline, if connected), start a protocol or start a playlist of protocols. Generally, the operation of the system is from this view and configuration of the system can be found elsewhere. In order to configure the protocols, which allow the user to control the visual scene and treadmill, the user utilizes the protocols page.

With continued reference to the illustrative embodiment of FIG. 4, further features of the workspace view graphical user interface 300 will be explained. From the Workspace page, the user can choose to display the quick controls for the instrumented treadmill. The quick controls will allow the user to run the treadmill independently from the motion base and/or the treadmill independently from the incline. The gear icon 338 on the Treadmill Control Card 306 opens the settings window of the treadmill (the treadmill settings will be described in further detail hereinafter). The connection status to both treadmill belts is shown in the Treadmill Control Card 306, such that when properly connected and ready to record (or currently recording) data, the status symbols 340 will be green, indicating a successful connection. If not, the status symbols 340 will be red, indicating an unsuccessful connection. If the incline is connected, the connection status of the incline is also shown, such that when properly connected and ready, the status symbol will be green, indicating a successful connection. If not, they will be red, indicating an unsuccessful connection. Also, if the treadmill is connected, it will say "Connected" at the title of the card 306 (e.g., see FIG. 4). If the treadmill is not connected, it will say "Not Connected" at the title of the card 306. On the Treadmill Control Card 306, there is a switch 342 that will synchronize the two treadmill belts when turned on. The treadmill belts will default to the left treadmill belt speed when turned on and the 'sync belts' switch 342 will turn green. When the treadmill belts are synchronized, the card will merge the left and right treadmill belt buttons to create a single velocity control input that controls both belts, still retaining the commit and toggle input types. When the switch 342 is off, there will be two columns for left and right belts separately. This will allow the user to control the velocity and the acceleration of the two belts separately.

Still referring to the illustrative embodiment of FIG. 4, the treadmill velocity controls will now be described. The current velocity of the treadmill is always being displayed on the Treadmill Control Card 306. The Treadmill Control Card 306 will show the actual velocity of the treadmill. When a new value of velocity is given in the quick controls section, the treadmill may take some time to reach that value, so in the meantime, the actual velocity of the treadmill can be tracked from this display (see FIG. 4). If the units are changed through the treadmill settings window, these texts will also change (the treadmill settings window will be described in further detail hereinafter). In the illustrative embodiment, there are two ways to control the velocity of the treadmill, namely (i) the standard quick style or (ii) the "commit" style. The quick treadmill velocity control 312 allows the user to manually increase or decrease the speed by set increments (see FIG. 4). The user can either type in the desired velocity and/or acceleration or he or she can use the up and down arrows to control the input. As soon as the value changes, the treadmill will adjust its velocity accordingly. When the belts are synchronized, these columns will merge the left and right treadmill belt buttons to create a single velocity control input that controls both belts, still retaining the commit and toggle input types. The increment for toggling the velocity and acceleration may be +/−0.1 units. The following unit options are available for velocity: (i) m/s, (ii) mph, and (iii) km/h. If the units are changed through the treadmill settings window, these texts will also change (the treadmill settings window will be described in further detail hereinafter). The acceleration will be in the same unit standard as the velocity, such that if the user sets the value for velocity to m/s, the acceleration will be displayed in $m/s^2$. The acceleration and the velocity values can be either clicked on and a new value manually entered through the keyboard, or the user can use the toggle to increment the acceleration values. As soon as the value changes, the treadmill will adjust its velocity accordingly.

In the illustrative embodiment, on the Treadmill Controls card 306, the lower of the two inputs is the commit style section 314. In this section, the user types in the desired velocity and selects the commit button to begin accelerating the treadmill to the new velocity. The desired acceleration can also be edited here by the user, but there is a default value that accelerates at a standard treadmill acceleration rate. The commit button can only be selected by clicking the mouse on it, the user cannot use the keyboard to activate the commit button (such as by tabbing it). The acceleration and the velocity values can be either clicked on and a new value manually entered through the keyboard, or the user can use the toggle to increment the acceleration values. When the Commit button is pressed a confirmation window will appear, asking the user to confirm his or her changes. When the belts are synchronized, these columns will merge the left and right treadmill belt buttons to create a single velocity control input that controls both belts, still retaining the commit and toggle input types. If the units are changed through the treadmill settings window, these texts will also change (the treadmill settings window will be described in further detail hereinafter). The Stop button 344 will bring the treadmill to a stop in a quick, yet safe manner. This stop button 344 affects the scene's velocity only if the scene-to-belt sync toggle in the Scene Settings card is enabled. Otherwise, it will only safely stop the treadmill.

In the illustrative embodiment, when the treadmill has an incline base, the current angle of the incline is always being displayed on the Treadmill Controls Card. This will show the actual angle of the incline base. When a new value of angle is given in the numeric box, it may take some time to reach that value, so in the meantime the actual angle of the base can be tracked from this display. In the "Incline" numeric box of the illustrative embodiment, a user types in the desired angle and selects the commit button to begin moving the incline base to the angle. The commit button can only be selected by clicking the mouse on it, the user cannot use the keyboard to activate the commit button (such as by tabbing it). The value can be given by either clicking on it and entering a new value manually through the keyboard or clicking on the up and down arrows to increment the value. When the Commit button is pressed a confirmation window will appear, asking the user to confirm their changes. If the user does not approve the changes, he or she can click the "X" button to close the window and change the desired values before applying. In the illustrative embodiment, when the Home button is clicked, the incline base moves to its home position that has been set in the advanced setting (the Incline Advanced Settings will be described in more detail hereinafter).

Next, the Motion Base Control Card 304 of the illustrative embodiment will be described with reference again to FIG. 4. From the workspace page, the user can choose to display the quick controls 308 for the motion base. The quick controls 308 allow the user to run the motion base independently from the treadmill. The gear icon 336 on the Motion Base Control Card 304 opens the settings window of the motion base (the motion base settings will be described in further detail hereinafter). The connection status to both motion base actuators are shown, such that when properly connected, the status symbols 346 will be green, indicating a successful connection. If not, the status symbols 346 will be red, indicating an unsuccessful connection. Also, if the motion base is connected, it will say "Connected" at the title of the card 304. If the motion base is not connected, it will say "Not Connected" at the title of the card 304. The current pitch and roll angles of the motion base is always being displayed on the Motion Base Control Card 304. This display will show the actual angle of the motion base. When a new value of angle is given in the quick controls section 308, it may take some time to reach that value, so in the meantime, the actual angle of the motion base can be tracked from this display. There are two ways to control the motion of the motion base, namely (i) the standard quick style or (ii) the "commit" style. The quick motion base control 308 of the Motion Base Control Card 304 allows the user to manually increase or decrease the angles by set increments. The user can either type in the desired angle or he or she can use the up and down arrows to control the input. As soon as the value changes, the motion base will adjust its position accordingly. In the illustrative embodiment, the increment for toggling the angles is +/−0.1 units. The values can be either clicked on and a new value manually entered through the keyboard, or the user can use the toggle to increment the acceleration values. As soon as the value changes, the motion base will adjust its angles accordingly. In the illustrative embodiment, the format is "00.0" for the input fields.

In the illustrative embodiment, on the Motion Base Controls Card 304, the lower of the two inputs is the commit style section 310. In the commit style section 310, the user types in the desired angle and selects the commit button to begin moving the motion base to the angle. The commit button can only be selected by clicking the mouse on it, the user cannot use the keyboard to activate the commit button (such as by tabbing it). The pitch and roll values can be either clicked on and a new value manually entered through the keyboard, or the user can use the toggle to increment the values. When the Commit button is pressed a confirmation window will appear, asking the user to confirm their changes. If the user does not approve the changes, they can click the "X" button to close the window and change the desired values before applying. The Stop button 348 will bring the motion base to a stop in a quick, yet safe manner. The Pause button 350 will pause the motion of the motion base. When clicked again the motion will continue from where it was paused. The Home button 352 will move the motion base to its set home position that is configured in the motion base advance settings window (the motion base settings will be described in further detail hereinafter).

The remote control functionality of the illustrative embodiment will now be described. In the illustrative embodiment, a user can use third party applications and custom programs to make use of the existing controls available in the software, such as basic treadmill commands such as start/stop, command velocity/acceleration, incline controls for start/stop and pitch angle, as well as provide access to the real time data stream. All the settings regarding the remote control can be accessed from the devices window (refer to "Devices" window description for further information). When enabled, the Remote Control toggle activates the Remote Control function and allows other applications to control the software. The controls of the devices are not be displayed on the software to prevent any damage to the hardware. The toggle has a "green" knob. When disabled, the toggle turns to default state so that all the controls can be done from the software and the toggle has a "red" knob. In the illustrative embodiment, the Remote Control interface includes a Server icon and a Client icon. When the connection with the server is unsuccessful, the Server icon will have a red circle with a cross inside of the circle. When there is a successful connection, the Server icon will have a green circle with a tick mark inside of the circle. When the connection with the client is unsuccessful, the Client icon will have a red circle with a cross inside of the circle. When there is a successful connection, the Client icon will have a green circle with a tick mark inside of the circle.

Referring again to FIG. 4, in the illustrative embodiment, the workspace user interface 300 contains a "Participant Monitoring" card 354, which shows the user information about the distance that a test subject has travelled and the steps that have been made by the test subject. The participant view contains: (i) a distance travelled counter, and (ii) a step counter. In the illustrative embodiment, the units of the distance travelled metric of the Participant Monitoring card 354 may be meters. The travelled distance value is saved in the output CSV file. Upon initiation of a new data collection, step counter resets to "0" steps. This value can be "zeroed" at any time. The user can click the "reset" button to zero the distance value. The step count is a global variable necessary for triggering events. On the participant display, it is displayed in real-time and counts the steps the participant takes during the trial. This value can be "zeroed" at any time. The user can click the "reset" button. The gear icon button 356 at the top of the Participant Monitoring card 354 opens the settings window for this card.

In the settings pop-up window for the Participant Monitoring card 354, the user is able to do the following: (i) select from a drop-down menu for which marker they will use for both the left foot and right foot, (ii) set a threshold value for each foot, and (iii) once these are all defined, the user will select 'Save' to commit. From this settings window, the user chooses markers for the left and right feet and defines a threshold to be used as steps. When the marker's position goes up to defined value it will count as a step and will be added to the Step Counter number in the participant view card 354 in the main view. The left foot section of the settings window defines the participant's left foot marker and creates a threshold value in height specially for the left foot, to be counted as a step. The left foot section of the settings window includes: (i) a first dropdown, (ii) a second dropdown, and (iii) a numeric input field. For the left foot, the list in the first dropdown comes from the motion capture software. The user can choose between a group of data to be defined such as marker, segment, joint, or device. For step, it is better to choose the marker option. For the left foot, the list in the second dropdown also comes from the motion capture software. Once the user chooses the group they will use, then he or she can specify which object in that group to use as the left foot. Transformation information of this object will be used to compare and count as the left step. For step, it is better to choose the marker that is attached to the participant's left foot. For the left foot, the numeric input field value defines the threshold for the left foot. So, whenever the object that is selected with the dropdowns, goes over this value (in height) the software will see this as a step that is made with the left foot. This value is in millimeters (mm). The right foot section defines the participant's right foot marker and creates a threshold value in height specially for the right foot, to be counted as a step. Like the left foot section, the right foot section of the settings window includes: (i) a first dropdown, (ii) a second dropdown, and (iii) a numeric input field. For the right foot, the list in the first dropdown comes from the motion capture software. The user can choose between a group of data to be defined such as marker, segment, joint, or device. For step, it is better to choose the marker option. For the right foot, the list in the second dropdown also comes from the motion capture software. Once the user chooses the group he or she will use, then he or she can specify which object in that group to use as the right foot. Transformation information of this object will be used to compare and count as the right step. For step, it is better to choose the marker that is attached to the participant's right foot. For the right foot, numeric input field value defines the threshold for the right foot. So, whenever the object that is selected with the dropdowns, goes over this value (in height) the software will see this as a step that is made with the right foot. This value is in millimeters (mm). When on the workspace page 300, the user sees the step counter incrementing (if someone is walking with the selected markers) in the Participant View card 354. The step counter value is saved in the output CSV file. Upon initiation of a new data collection, step counter resets to "0" steps. If depressed by the user, the reset button of the Participant Monitoring card 354 will instantly reset to zero the distance traveled and the step counter. Then, the counters will immediately resume counting. When a new trial begins recording, the distance traveled, and the step counter will automatically be zeroed.

With continued reference to the illustrative embodiment of FIG. 4, the Data View Card 302 of the workspace user interface 300 will now be explained in detail. The data view card 302 is where the user can see the live data streaming from the force devices. The data view card 302 displays any of the force channels using checkbox. The connection status indicators 358 to the motion capture device and the treadmill is shown, such that when properly connected and ready for capturing the status symbols 358 will be green, indicating a successful connection. If not, the status symbols 358 will be red, indicating an unsuccessful connection. The zero button 360 in the data view card 302 resets the values of the treadmill force plates to zero. The treadmill graph view 320, 322 will capture live data from the treadmill and will scroll focusing on the end of the signals, showing the signals from the treadmill channels as they are generated and periodically re-setting the scale, so only a specific window of time is shown. The chart will auto-scale in the y-axis to the largest value of the channels that are available during live data capture mode. As the recording continues, the scrollbar at the bottom will naturally shrink (due to the duration of the trial). The scrollbar will be fixed to the end. If the user moves the x-axis scrollbar, the movement of the graph (sliding to the end motion) will stop. If the user moves the scrollbar to the end, the graph will continue to move automatically focusing on the end of the signals. In the illustrative embodiment, the user can only use the zoom feature in the post-process mode. After the recording is finished, it can also be viewed by using the scrollbars and/or zoom buttons. When a trial is finished, the data is visible in the data view. For navigation, the user can use the scroll bars to scroll up/down and left/right on the data set. By pressing and holding the mouse wheel down and moving the mouse, the window will move in the direction of the mouse, similar to CAD programs and other similar software. The user can click +/− to zoom in and out or select the zoom icon and click and drag a rectangular area of the chart to zoom into if the data is not live. Otherwise, it will auto-scale as the data plots. From the Display-in section of the Data View Card 302, the user can choose what units he or she wants to view the data in, selected from: (i) Newtons (default), (ii) Pounds, and (iii) Kilograms. Each of the treadmill data channels can be toggled on or off with toggle buttons in the display. A list of the available channels is populated next to the chart, clicking the toggle button from "off" to "on" causes the real-time data stream to be displayed for the individually selected channel with the color of the selected button. Toggling off the channel causes it to disappear from the chart.

In one or more embodiments, the Data View Card 302 of the workspace user interface 300 may further include a unit dropdown menu for determining whether Imperial or Metric units will be used for displaying the data. In these one or more embodiments, from the Display in section, a user can choose what units they want to use in the software, namely either (i) Metric (default) or (iii) Imperial.

In the illustrative embodiment, the motion base graph view will capture live data from the motion base and will scroll focusing on the end of the signals, showing the signals from the motion base channels as they are generated and periodically re-setting the scale, so only a specific window of time is shown. The chart will auto-scale in the y-axis to the largest value of the channels that are available during live data capture mode. As the recording continues, the scrollbar at the bottom will naturally shrink (due to the duration of the trial). The scrollbar will be fixed to the end. If the user moves the x-axis scrollbar, the movement of the graph (sliding to the end motion) will stop. If the user moves the scrollbar to the end, the graph will continue to move automatically focusing on the end of the signals. In the illustrative embodiment, the user can only use the zoom feature in the post-process mode. After the recording is finished, it can also be viewed by using the scrollbars and/or zoom buttons. When a trial is finished, the data is visible in the data view. For navigation, the user can use the scroll bars to scroll up/down and left/right on the data set. By pressing and holding the mouse wheel down and moving the mouse, the window will move in the direction of the mouse, similar to CAD programs and other similar software. The user can click +/− to zoom in and out or select the zoom icon and click and drag a rectangular area of the chart to zoom into if the data is not live. Otherwise, it will auto-scale as the data plots. Each of the motion base data channels can be toggled on or off with toggle buttons in the display. A list of the available channels is populated next to the chart, clicking the toggle button from "off" to "on" causes the real-time data stream to be displayed for the individually selected channel with the color of the selected button. Toggling off the channel causes it to disappear from the chart.

In the illustrative embodiment, the COP view 362 is at the bottom of the Data View Card 302 and shows the COP from the treadmill belts (left/right). The user can choose to view combined (total) COP (as shown in FIG. 4) or the separate COP from each treadmill belt using the COP View dropdown. When the combined is selected, there will be one (1) set of coordinates displayed under the dropdown and one (1) point visible on the treadmill. When the separate is selected, there will be two (2) sets of coordinates displayed under the dropdown and two (2) points visible on the treadmill, one for each belt.

Now, the specific attributes of the protocol builder card 222, 324 illustrated in the workspace view graphical user interface 200, 300 of FIGS. 2 and 4 will be described in more detail. In the illustrative embodiment, the protocol builder card 222, 324 in the workspace page 200, 300 is used by the user to select, order, and run pre-configured protocols. As will be described hereinafter, in order to create or edit protocols the user goes to Protocols page 600 (see FIG. 7). The default view of this card 222, 324 is the "queue" which shows the upcoming protocols to be run. The user can drag and drop protocols from the List of Protocols view, which can be viewed by expanding the queue view. In the illustrative embodiment, the protocol playlist is the "queue" for protocols to be run. The user will set up the specific parameters of the protocol prior to loading them into the queue. The queue will then create a playlist, where the user can run multiple protocols in a single session (single or multiple trials). In one embodiment, recording of the data is done separately from this queue. For example, it can be manual or time-based (as will be explained hereinafter in conjunction with Capture Settings). In FIGS. 2 and 4, no protocols have been established yet in the queues.

In the illustrative embodiment, if there is a certain playlist that has been added to the queue, the name of the playlist will be under the "Protocols" title. If no playlist that has been added to the queue, it will just say "Custom" under the "Protocols" title. The selection of the "Clear All" button in the protocol builder card 222, 324 by the user removes all the protocols in the queue. As shown in FIGS. 2 and 4, if the queue is empty, there is a notification saying, "No protocol to show in queue." and there is an "Add Protocol" button 224, 326 that acts the same way as "More" button 226, 328 at the end of the card, which expands the card showing a list of all the protocols. When expanded and the queue is empty, there will be a notification saying, "Click and drag the protocol to add to queue". When protocols are added to the queue, the order can be changed by clicking and dragging up and down the queue. The protocols can also be removed individually using the "X" button at the end of the protocol buttons, except the protocol which is being played. In the illustrative embodiment, each protocol displays its own name and has an icon that gives the number of repetitions for the protocol. For example, the protocol display image may inform the user that a protocol (e.g., named "Protocol 0") will repeat two times once the protocol starts. When the queue starts, the active protocol is designated differently than the non-active ones (e.g., by change in color) and a process bar is displayed indicating an estimated time of the protocol so that the user is able to easily track which protocol is being played. Once the protocol plays, the number of displayed repetitions decreases, and the loading bar will start from the beginning.

In the illustrative embodiment, referring again to FIGS. 2 and 4, if the queue is empty, the player buttons 228-232 and 330-334 will be disabled. The Play button 228, 330 starts playing the queue following the order in the queue, and the button itself will turn into a stop button when the queue is being played. If there are any capture settings in the protocols in the queue, the stop button will also stop the recording. The Next and Previous buttons 230, 232 and 332, 334 changes the protocol that is being played according to the order in the list. When a protocol or protocols are added to the list, the remaining time section will be visible and display the time that remains until the queue is finished. In the illustrative embodiment, the user is able to click and drag protocols from the left side to the right, adding them to the queue. When a protocol is clicked twice, the software opens the setting page of that protocol. The expanded version of the protocol card 222, 324 is at the top layer, and covers the other elements of the workspace. As a default, the software shows all the protocols. The user is able to filter the protocol list using a dropdown menu. The dropdown menu has the options of: (i) All, (ii) Favorites, (iii) Playlists, (iv) Stability, (v) Agility, (vi) Mobility, (vii) Vision, and (viii) Cognition.

In the illustrative embodiment, a "Create New" button is provided to open the protocol creation page (see Protocol Settings for more information), allowing user to quickly create a new protocol.

In the illustrative embodiment, on the workspace page (see FIG. 2), there is a button 220 for Capture Settings at the bottom bar, that opens the Capture Settings pop-up. The Capture Settings pop-up window has the following features: (i) a File Name Input Field, which defines the name of the output file (all the files will be in (.csv) format); (ii) an Auto-Increment Toggle, which controls whether the file name will be incremented on every new capture (on/off); (iii) a Save Path Input Field, which defines where the output file will be saved locally; (iv) Browse Button, which opens a file dialogue for easily choosing the location of the output file; (v) a Timer, which includes an (a) Enable Timer Checkbox that controls if the capturing will be controlled by time, and (b) a Timer Interval Spinner, that defines after how many seconds the capturing should stop when the timer is enabled; (vi) a Sync Capture with Protocols toggle, which syncs the capturing with the protocol queue (i.e., it starts recording when queue starts and stops when it stops); (vii) a Save Button, which saves all the changes that have been made in the capture settings window; and (viii) a Cancel Button that, if any changes were made, reverts the changes back and closes the window. In the illustrative embodiment, the data output file may be provided with a timestamp that includes hours, minutes, seconds, and milliseconds.

In the illustrative embodiment, pressing the "Start/Stop Recording" button 218 at the bottom bar in the main page 200 causes the data from the connected devices to start capturing (recording). If the file name and the file save path are not configured in the capture settings window, an error window message will appear and prevent the data capturing without it. The error window is able to be closed using either the "X" button or the "OK" button. After defining a file name and a save path, the recording starts, and when recording, the "Start Recording" button 218 will change to a stop button and there will be "Recording . . . " text 236 displayed at the bottom bar. Hitting the stop button 218 will stop the recording of data to a file and increment the file name, such that when the capture button is pressed again, the name of the trial will not override the previous trial. It does not affect the protocol playlist, the motion base operation, or the treadmill operation, only data capture. If the capture settings have the option of timer and time interval enabled, information of the interval and remaining time will be displayed on the bottom process bar. The bottom capture bar will be visible if a recording has started. So, when the user goes to Protocols page, they can stop the recording or be informed of the time and process. When recording starts, the name of the trial is displayed in the bottom bar in the main view (e.g., below the "Recording . . . " text 236—see FIG. 2).

In the illustrative embodiment, the Step window can be accessed from the Step button in the Participant view card in main view 200. From this window, the user is able to configure the specific markers to be used in the scene settings. In this window, the "Save Button" saves any changes that have been made in the Step Window and closes the window. In this window, the "Cancel Button" reverses any changes that have been made in the Step Window and closes the window.

In the illustrative embodiment, when a Remote PC is selected from the Available Devices section of the "Devices" window, the Remote PC device will be added to the list. From here, a user can configure a remote personal computer (PC) that allows them to use the software remotely. After the user clicks "Save", the Available Devices section of the "Devices" window will be closed. When the Remote PC is clicked on by the user, its configuration will be visible in the Device Configuration section of the "Devices" window. The Device Configuration section for the Remote PC includes: (i) a Remote IP input field, (ii) a Remote Port input field, and (iii) a RPC Port input field. The Remote IP input field value defines the IP of the system that will have remote access to the software. The Remote Port input field value defines the port of the system that will have remote access to the software. The RPC Port input field value defines the RPC port of the system that will have remote access to the software.

Next, with continued reference to FIG. 2, the treadmill settings functionality will be described. In the illustrative embodiment, when the treadmill is selected from the Available Devices section of the "Devices" window, the Treadmill device will be added to the list. From here, a user can configure the treadmill. After "Save" is clicked by the user, the Available Devices section of the "Devices" window will be closed. When the user clicks on the Treadmill, its configuration will be visible in the Device Configuration section of the "Devices" window. In one or more embodiments, the gear icon 238 on the Treadmill Control Card 204 may also open the settings window for the treadmill. In the Device Configuration section of the "Devices" window, if the treadmill is selected, the following options will appear: (i) Firmware Version text, which displays the version number of the firmware on the treadmill, (ii) Firmware Date text, which displays the date of the last update on the firmware on the treadmill, (iii) Allow Opposite Velocities toggle, which enables the option to input opposite direction while inputting velocities for each belt; (iv) Max Forward Velocity Numeric Input Field (m/s), which defines the max number that can be given in the forward direction of velocity in treadmill controls card in workspace; (v) Max Backward Velocity Numeric Input Field (m/s), which defines the max number that can be given in the backward direction of velocity in treadmill controls card in workspace; (vi) Max Acceleration Numeric Input Field (m/s$^2$), which defines the max number that can be given to acceleration value in treadmill controls card in workspace; (vii) Max Deceleration Numeric Input Field (m/s$^2$), which defines the max number that can be given to backward acceleration value in treadmill controls card in workspace; and (viii) Belt Velocity Step Numeric Input Field (m/s), which defines the increment and decrement amount of the (+) and (−) buttons in the Treadmill Controls Card 204 in the workspace. In one or more embodiments, the Device Configuration section of the "Devices" window may include the following additional options for the treadmill: (i) Velocity Units Dropdown, which controls the velocity units of the treadmill and has three options: (a) m/s, (b) mph, and (c) km/h; and (ii) Acceleration Units Dropdown, which controls the acceleration units of the treadmill and has two options: (a) m/s$^2$, (b) km/h$^2$. In the illustrative embodiment, the Device Configuration section of the "Devices" window for the treadmill further includes: (i) a "Reset" button, which restores all the changes to default when pressed by a user, (ii) a hamburger menu, which accesses the advanced settings for the treadmill, (iii) a "Save" Button, which saves any changes that have been made in the Step Window and closes the window; and (iv) a "Cancel" Button, which reverses any changes that have been made in the Step Window and closes the window. In the illustrative embodiment, the hamburger menu (i.e., collapsed menu icon) reveals more options such as the Advanced Settings option, which opens the advanced settings pop up for the treadmill.

In the illustrative embodiment, the treadmill advanced settings are accessed by clicking on the Advanced Settings option on the hamburger menu of Treadmill Settings screen. The Advanced Settings window is intended for the technicians that are assigned by the device manufacturer. When clicked an error dialog window will appear to warn the user. In Advanced Settings, if the treadmill is selected and connected, the following options will appear: (i) Left Speed Factor Numeric Input Field, (ii) Right Speed Factor Numeric Input Field, (iii) Motor Pulley Diameter Numeric Input Field (mm), (iv) Roller Pulley Diameter Numeric Input Field (mm), (v) Roller Diameter Numeric Input Field (mm), (vi) Belt Thickness Numeric Input Field (mm), (vii) Belt Feed Constant (mm/rev), (viii) Left Feed Constant (mm/rev), (ix) Right Feed Constant (mm/rev), (x) Max Forward Speed (mm/s), (xi) Max Backward Speed (mm/s), (xii) Max Acceleration (mm/s$^2$), and (xiii) Max Deceleration (mm/s$^2$). When cancelled all the changes that have been made will be reversed. When save is clicked, a notification will appear so as to get confirmation from the user. When the user clicks "Yes" on the confirmation window, the software will save and apply all the changes and close the window. When the user clicks "No" on the confirmation window, the software will not save the changes.

Next, the incline settings functionality will be explained. In the illustrative embodiment, when treadmill with incline is selected from the Available Devices section of the "Devices" window, the Treadmill and the Incline devices will be added separately to the list. From here, a user can configure the treadmill and the incline. After clicking the "Save" button, the Available Devices section will be closed. When the user clicks on the Incline, its configuration will be visible in the Device Configuration section of the "Devices" window. In the Device Configuration section of the "Devices" window, if the Incline is selected, the following options will appear: (i) a Max Angle input field (in degrees), which defines the maximum number that can be given to an incline angle value in the Treadmill Controls Card 204 in the workspace; (ii) a "Reset" button, which restores all the changes to default, (iii) a hamburger menu, which accesses the advanced settings (the advanced settings open the advanced settings pop up window); (iv) a "Save" button, which saves any changes that have been made in the Step Window and closes the window; and (v) a "Cancel" button, which reverses any changes that have been made in the Step Window and closes the window.

In the illustrative embodiment, the incline advanced settings are accessed by clicking on the Advanced Settings option on the hamburger menu of Incline Settings screen. The Advanced Settings window is intended for the technicians that are assigned by the device manufacturer. When clicked an error dialog window will appear to warn the user. In Advanced Settings, if the treadmill with incline is selected and connected, the following incline options will appear: (i) Position Actual text (mm), which displays the actual position; (ii) Position Input field (in revs), which defines the value of the position input; (iii) "Set Position" button, which sets the position as defined above; and (iv) "Set Home" button, which sets the position as the home position. In the Position Input field, the "−5" button decrements the position input value by −5 on every click, the "−1" button decrements the position input value by −1 on every click, the "−0.25" button decrements the position input value by −0.25 on every click, the "0.25" button increments the position input value by +0.25 on every click, the "+1" button increments the value by +1 on every click, and "+5" button increments the value by +5 on every click. The user can either input their desired value or increment the value using the +/− buttons. When cancelled, all the changes that have been made to the advanced settings by the user will be reversed. When the "Save" button is clicked by the user, a notification will appear to get confirmation from the user. When "Yes" is clicked by the user on the notification, the software will save and apply all the changes and close the window. When "No" by the user is clicked on the notification, the software will not save the changes.

Now, turning to FIG. 4, the motion base settings functionality will be explained. In the illustrative embodiment, when Treadmill and Motion Base is selected from the Available Devices section of the "Devices" window, the Treadmill and the Motion Base devices will be added to the list. From here, a user can configure the treadmill and the motion base. After clicking the "Save" button, the Available Devices section of the "Devices" window will be closed. When the Motion Base is clicked on by the user, its configuration will be visible in the Device Configuration section of the "Devices" window. In one or more embodiments, the gear icon 336 on the Motion Base Control Card 304 may also open the motion base settings window. In the motion base settings window, the following options will appear: (i) Max Angular Velocity numeric input field in deg/s, which defines the maximum velocity of the motion base; (ii) Max Angular Acceleration numeric input field in deg/s$^2$, which defines the maximum angular acceleration of the motion base; (iii) Max Time numeric input field in seconds, which defines the maximum time for the motion of the motion base; (iv) Pitch Step numeric input field in degrees, which defines the increment and decrement amount of the (+) and (−) button of the pitch angle in motion base control card; (v) Roll Step numeric input field in degrees, which defines the increment and decrement amount of the (+) and (−) button of the roll angle in motion base control card; (vi) "Reset" button, which restores all the changes to default; (vii) the hamburger menu, which accesses the advanced settings button; (viii) "Save" button, which saves any changes that have been made in the Motion Base Settings Window and closes the window; and (ix) "Cancel" Button, which reverses any changes that have been made in the Motion Base Settings Window and closes the window. The hamburger menu reveals the "Advanced Settings" button, which opens the advanced settings pop up.

In the illustrative embodiment, the Motion Base Advanced Settings are accessed by clicking on the Advanced Settings option on the hamburger menu (i.e., collapsed menu icon) of Motion Base Settings screen. The Advanced Settings window is intended for the technicians that are assigned by the device manufacturer. When clicked, an error dialog window will appear to warn the user. The Advanced Settings for the motion base contains a warning label, which informs the user that: "Changing the actuator positions will cause the motion base to move. Ensure the area around the motion base is clear and no one is using the device before using these controls." This warning notifies the user that any changes that are made in this section will move the motion base. In Advanced Settings for the motion base, the following options will appear: (i) Actuator Dropdown, which controls the type of actuator to be configured, and has the options of: (a) Left Actuator and (b) Right Actuator (choosing one of these will change the controls underneath accordingly); (ii) Left/Right Position Actual Display in millimeters (mm); (iii) Left/Right Position Input numeric input field in millimeters (mm) that includes: (a) a "−10" button that decrements the value by −10 on every click, (b) a "−1" button that decrements the value by −1 on every click, (c) a "−0.1" button that decrements the value by −0.1 on every click, (d) a "+0.1" button that increments the value by +0.1 on every click, (e) a "+1" button that increments the value by +1 on every click, and (f) a "+10" button that increments the value by +10 on every click (the user can either input their desired value or increment the value using the +/− buttons); (iv) Set Position button moves the motion base according to given values; (v) Set Home button: will set the current position of the motion base as the home position (when the home button on the motion base control card 304 is selected, the motion base will move to this position); and (vi) Polygon Limit Section, wherein this area defines the maximum values of the motion base's corners in pitch and roll values, and includes: (a) a Reset Button that resets the changes to its original version, (b) a Save Button that saves the changes that have been made in the Polygon Limit section and closes the window (it will not affect the actuators section), and (c) a Cancel Button, which reverses any changes that have been in the Polygon Limit section, and closes the window. The Cancel Button of the Polygon Limit section will not affect the actuators section. When cancelled, all the changes that have been made will be reverted back to the original settings. When "Save" is clicked in the Advanced Settings for the motion base, a notification will appear as to get confirmation from the user. When the user clicks "Yes" on the confirmation window, the software will save and apply all the changes and close the window. When the user clicks "No" on the confirmation window, the software will not save the changes.

In the illustrative embodiment, the Protocols page is where the user can access all the protocols. All functionality related to the protocols are done from here, like creating a protocol, editing a protocol, creating playlists and so on. With reference to FIGS. 2 and 4, the Queue section will be reflected in the protocols card 222, 324 in the Workspace page 200, 300. The user can add protocols from the list of protocols by clicking and dragging them to the queue. The user can change the order in the queue with the same method (click & drag). The user can remove the protocols in the queue individually by clicking the "x" button or clear the list with the "Clear All" button. When a protocol is added to the queue, a repeat section will appear on the protocol row. The value will define the number of repetitions the selected protocol will go through when the playlist starts. When a protocol is added to queue, a heart icon and the play buttons will be enabled. When the play button is activated, the Protocols page will change to Workspace page, with the queue started. The heart icon will save the protocols in the queue to Playlists section when pressed. The Playlists section stores the queues that the user saves. The playlist's name can be changed directly from its original name. If the user does not change the name, it will have names like Playlist1 and increase as they save more. The saved playlist can be deleted with the "x" button next to it or they can clear all the playlists by "Clear All" button. In that case, there will be a dialogue saying, "Are you sure?" and asks the user for confirmation. When a playlist is dragged into the queue, each protocol inside the playlist will be visible in the queue. The list of protocols shows all the protocols that are in the software. The All Protocols dropdown filters the protocol that shows on the list. The options, just like the one in the Protocols card on the Workspace page, will be as follows: (i) All Protocols, (ii) Favorites, (iii) Playlists, (iv) Stability, (v) Agility, (vi) Mobility, (vii) Vision, and (viii) Cognition. The search section will allow users to search for Protocols by their name. When the user starts typing a word, the list will automatically update accordingly, such as if they were to type "S" then the list will show only the protocols that start with the letter "S". There is a hamburger menu at the corner of each protocol that will reveal more options such as: (i) Edit, which opens the protocol settings page for that selected protocol (users can edit the protocol's configurations from here); (ii) Add to Fays, which marks the selected protocol as favorite (it will be added to the favorite list, which can be found through filtering the protocol list with Favorites selected from the dropdown options, and there will be a heart icon displayed on the corner of the protocol); (iii) Share, which opens the share window and let the user share this protocol with their patients and colleagues; and (iv) Delete, which deletes the selected protocol from the software. The "Create New" button at the bottom of the list of protocols, lets the user create a new protocol and opens the Protocol Builder screen.

Figure 7:
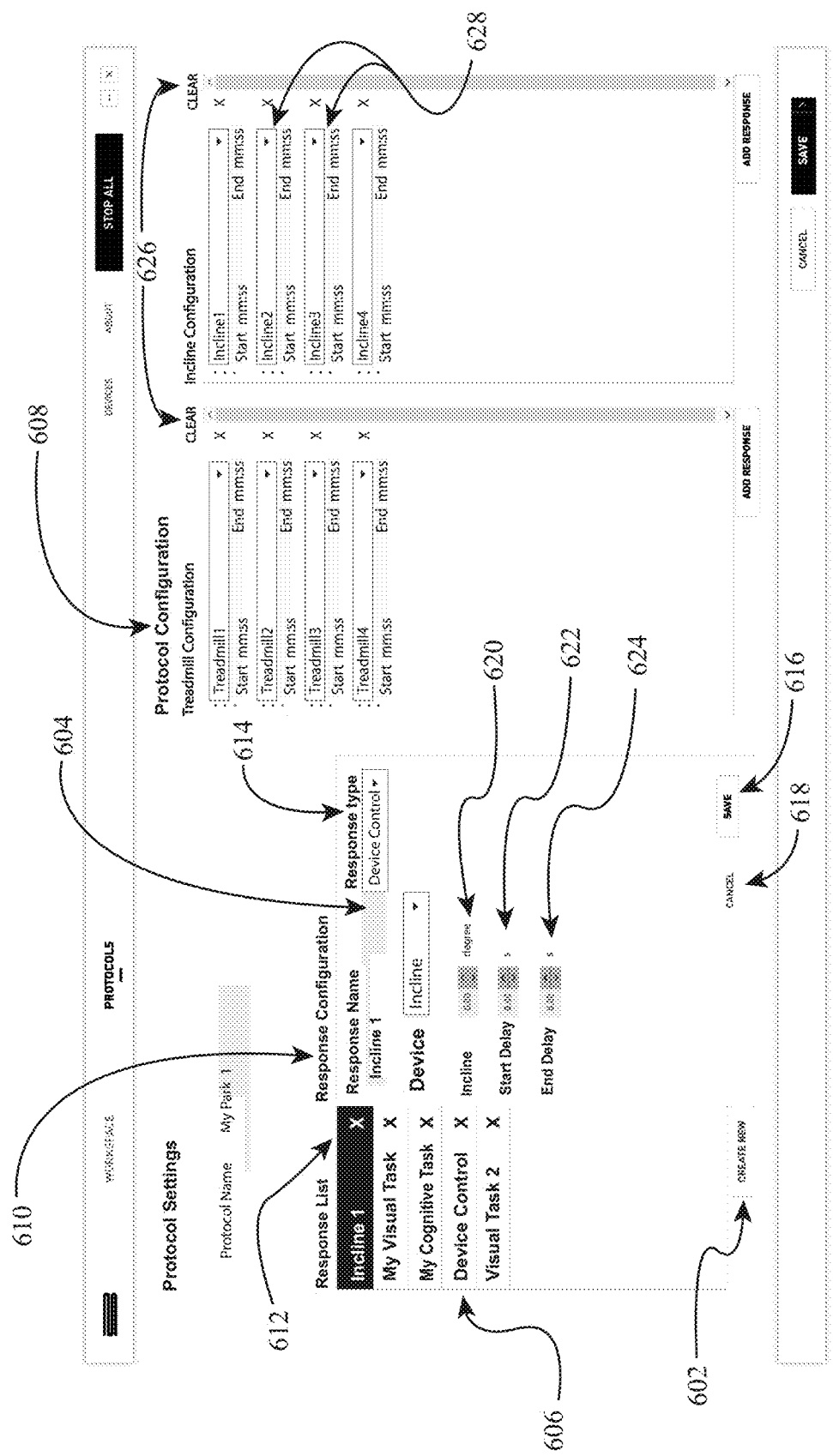
FIG. 7 is a sixth screenshot displayed on a user visual display device of a measurement and testing system illustrating the protocol view of the software, according to an embodiment of the invention.

According to another aspect of the illustrative embodiment, with reference to FIG. 7, the data processing device 160 of the measurement and testing system 100 is configured and arranged to generate a protocol builder graphical user interface 600. The protocol builder functionality occupies a separate "tab" in the software (see FIG. 7) so as to allow the user to configure customized protocols of the system. Advantageously, the protocol builder allows the user to create custom device responses in a list that are able to be saved and used as an experimental protocol. For example, a user may have a study where he or she needs someone to walk at a given speed for 2 minutes, then increase the speed so that they run for 4 minutes, and then lower back to walking speed again for 2 minutes before stopping. The protocol builder graphical user interface 600 allows the user to configure the software to perform those speed changes at the times specified, and the user only has to click "Play" once. As such, the protocol builder functionality allows for a very repeatable process for performing experiments where the user often does the exact same thing across many subjects. Additionally, the user is able sync the data capture to these protocols so the customized protocol is able to provide a one-click solution for performing an experiment with data collection once configured.

In the illustrative embodiment, whenever the user selects "Create New" or edit an existing protocol, the protocol builder view appears. The protocol builder view replaces the protocol page view, and the user can toggle back and forth between the workspace and the protocol builder view. The view exits to the protocol builder page once the protocol is saved or cancelled.

In the illustrative embodiment, a protocol is the collection of one or more responses. The protocol executes the predefined responses that are added to its configuration sections. In the Protocol Settings view (see e.g., FIG. 7), the user will create responses by selecting the "Create New" button 602 on the bottom left of the screen 600. In the illustrative embodiment, one type of response may comprise "Device Control". From there, the type of device to be controlled is selected by the user. For example, in one or more embodiments, either "treadmill", "incline", or "motion base" may be selected. Then, the options for the specific device that is selected will then populate the card.

In the illustrative embodiment, each new response will be given a unique name. When the response is configured, the user will input the desired name for the response (input box 604 at top of card). If no name is inputted, the name will automatically be incremented based on the type of response. For example, if there is no name given by the user, the default name would be "Device Control 0001" and the number scheme will add one digit for each new task where the default name has not changed, i.e., "Device Control 0002" and "Device Control 0003."

In the illustrative embodiment, each time a response is added, the response populates the "Response List" 606, shown on the left-hand side of the screen 600 in FIG. 7. These responses can then be put inside a protocol by using the protocol configuration 608 on the right side of the screen 600. When a response is selected from the list of responses 606, it will appear on its right, in Response Configuration section 610. From there, the user is able to change the name by typing a new name into the title or change any of the parameters within the response. These responses are global and can be used throughout all the protocols and they are displayed in the protocol configuration section 608 when selected for a particular protocol.

Turning again to the illustrative embodiment in FIG. 7, when the "X" button 612 on the right side of the response is pressed, it will delete the selected response. If the response selected for deletion is used in any other protocol, a warning window will appear notifying this action may cause other protocols to be invalid. Affected protocols are listed in that warning window. In the warning window, the selection of the "Yes" button by the user will continue with the deleting of the selected response and open another warning window. The selection of the "No" button by the user in the warning window will cancel the deleting action, close the warning window and stay in the protocol settings page. In the warning window, the selection of the "X" button will cancel the deleting action, close the warning window and stay in the protocol settings page. If the user clicked "Yes", the software will check to see if this action causes any other protocols to be not valid and notify the user which protocols are affected by this action in another warning window. In this additional warning window, the selection of the "OK" button or the "X" button by the user will close the warning window and stay in the protocol settings page. If there is any protocol that is not valid at the end of this process, the related protocol will have a warning icon next to the protocol in the List of Protocols section. When hovered over with mouse, the icon will pop up a notification text saying "The protocol is not valid. This could be due to a removed response from the protocol configuration. Please update this protocol." In order to use those protocols, the user should edit the responses used in those protocols.

In the illustrative embodiment, when the user clicks the "Create New" button 602 under the Response List 606, a new response will be added to the list and its parameters will be defined in the Response Configuration section 610. When an existing response is selected, its parameters will be visible under Response Configuration 610 and can be edited from here. Some of the options in the Response Configuration section 610 can change when the response or device type changes. Although, the options that stay the same in the Response Configuration section 610 are: (i) Response Name input field 604 where the user can define the name of the response, (ii) Response Type dropbox 614 where the user can change the type of the selected response (e.g., Device Control), (iii) Save button 616 where the depressing thereof saves the changes in the Response Configuration section 610 for the selected or created response, and (iv) Cancel button 618, which reverses any changes that have been made to the selected response or reverses the creation of a new response.

In the illustrative embodiment, when the Device Control type is selected by the user from the dropdown menu 614 (see FIG. 7), another dropdown menu appears, letting the user choose between devices. For example, in device dropdown menu 614, the user can choose the device for which he or she is going to create the response, such as: (i) incline, (ii) treadmill, and (iii) motion base. The Response Configuration section 610 is where the user defines a device response to be used in the protocols. For example, referring to FIG. 7, if the device is an incline device (e.g., inclined treadmill), the device input parameters may include: (i) Incline numeric input field 620 in degrees, which defines the incline of the device (e.g., inclined treadmill); (ii) Start Delay numeric input field 622 in seconds, which defines how many seconds later to start the response; and (iii) End Delay numeric input field 624 in seconds, which defines how many seconds it will stay at the target value after it reaches the target value. As another example, if the device is a treadmill, the device input parameters may include: (i) Sync Belts toggle, which when disabled, the left and right treadmill belts are shown separately to allow the user to control them separately, and when the sync is enabled, the two belt options are merged into one and it allows the user to control the belts at the same time; (ii) Velocity numeric input field in m/s, which defines the target velocity of the treadmill belts; (iii) Acceleration numeric input field in $m/s^2$, which defines the desired acceleration for the target velocity; (iv) Start Delay numeric input field in seconds, which defines how many seconds later to start the response; and (v) End Delay numeric input field in seconds, which defines how many seconds it will stay at the target values after it reaches the target values. As yet another example, if the device is a motion base, the device input parameters may include: (i) Pitch Angle numeric input field in degrees, which defines the target angle of pitch of the motion base; (ii) Roll Angle numeric input field in degrees, which defines the target angle of roll of the motion base; (iii) Acceleration numeric input field in $deg/s^2$, which defines the desired acceleration for the target velocity of the motion base; (iv) Velocity dropbox, which allows the user to choose a defined velocity or time for the selected response (changing of the option also changes the unit of the field, i.e., Velocity numeric input field in deg/s defines the velocity of the movement, while Time numeric input field in seconds defines the time it should take to complete the movement); (v) Start Delay numeric input field in second, which defines how many seconds later to start the response; and (vi) End Delay numeric input field in seconds, which defines how many seconds the motion base will stay at the target values after the motion base reaches the target values.

Referring again to FIG. 7, in the illustrative embodiment, the Protocol Configuration panel 608 is where the protocol is created. This section 608 will be auto-populated in relation to the devices that are connected to the system. For example, as shown in FIG. 7, the Protocol Configuration panel 608 displays two sections: (i) Treadmill Configuration and (ii) Incline Configuration. Each configuration list goes according to their order. Once one of them is completed, the other one starts. Although, the two lists are parallel with each other, so there can be simultaneous treadmill and incline responses or actions. However, there can never be two of the same device response simultaneously. In FIG. 7, when the "Clear Button" 626 is clicked by a user, all of the responses 628 in the related configuration list are cleared. When a new response is added by a user to the list, a blank response is created in the list. If there is more than one response on the list, the system will validate the combination of the responses. If there is something wrong with the movement combination, troubled movements will be highlighted, indicating the error. If the error is not corrected, the protocol cannot be saved or performed later. In the Protocol Configuration panel 608, the response dropdown selection allows the user to choose which response to use in that order. The Start Time Display in the Protocol Configuration panel 608 shows the time when the selected response is going to start once the protocol starts. This value is generated from the parameters inside the response and the responses that occur before it. The End Time Display in the Protocol Configuration panel 608 shows the time when the selected response is going to end once the protocol starts. This value is generated from the parameters inside the response and the responses that occur before it. In the Protocol Configuration panel 608, the "X" button removes that selected response row from the list. When the "Add Response" button is clicked in Protocol Configuration panel 608, a new and empty response will be added to the bottom of the selected list.

Now, an illustrative manner in which a user may build and utilize a protocol will be explained. The building and utilization of a protocol will be explained hereinafter in the following sections: (i) how to create a protocol, (ii) how to create a response, (iii) how to add a protocol to a queue, and (iv) how to perform the protocol and record the session. First of all, in order to create a protocol, after opening the software, a user first proceeds to the Protocols page by pressing the Protocols button located on the top bar 240 (see FIG. 2). After which, the user will see the Protocols page open. Once the Protocols page opens, the user clicks the Create New button at the end of the List of Protocols, which opens the Protocol Settings page. Initially, the user gives a name for this Protocol from the Protocol Name section.

In the illustrative embodiment, the protocols are created from responses. That is, one can think of responses as words and a protocol as a sentence. Thus, to form a sentence a user needs at least one word, and these words can be used to create different sentences. This means that a user has to create a response and this response can be used in different protocols. To create a new response, the user clicks the "Create New" button located at the bottom of the Response List (see e.g., the "Create New" button 602 is FIG. 7). When the "Create New" button is clicked, the settings of a new response will be displayed on the response configuration section on the right. If, for example, the only device configured in the software is the treadmill with incline, only the device control responses for the inclined treadmill are visible, and the inclined treadmill is set as the device. As such, these are automatically selected. As explained above for the treadmill, the sync belts toggle will synchronize the controls and the inputs of the belts for that particular response. The user can set velocity and acceleration values for the belts from the first two numeric boxes. The user can either click and type a new value using the keyboard or click the up and down arrows to increment to the desired value. As one example, both belts could be given a velocity of 2 m/s and an acceleration at $1 m/s^2$. Then, the user could enter a delay value for that specific response and define how long this state of the treadmill should last in the stay for numeric box. As one example, suppose that this response is made to start after 3.0 seconds and continue for 10.0 seconds. This means after reaching that state, the treadmill belts will keep their values for 10 seconds. And then, the user can give a name to the response from the Response Name Input Field. For example, the response could be named "TM 1", and then the user could click "Save" button to save the response. After pressing "Save", the user should see that the selected response is closed from the Response Configuration section and there is a new Response named "TM 1" in the Response List section. When a user clicks on it, he or she should see all the settings of that response in the Response Configuration section.

Now, that the user has created his or her response, he or she can use it in a protocol. In order to add that response to the created protocol, he or she clicks the "Add Response" button that is located at the bottom of the Protocol Configuration section. The user should see a new line has been added to the Protocol Configuration. This line represents the first response, first action in this protocol. The dropdown allows the user to choose between other responses located in the software. In this example, because the user has created only one response, the list only has the "TM 1" response therein. If the user were to create more, the user should see all of the responses on that dropdown. But for this example, the focus will just be on the initial protocol. After adding the response, the user will see the start and end times under that dropdown as "Start 00:03:00" and "End 00:15:00". This means that once the protocol starts this "TM 1" response will start at the 3rd second and end at 15th second into the protocol. In the illustrative embodiment, the response that was added will also be colored "red". This is because the protocol cannot be performed safely yet. All the protocols should end at a stop position for them to be safe. As such, the user needs to create a stop response for the treadmill with the same method. Then, the user should add this response to the end of the Protocol Configuration section. This time, once the user clicks the "Add Response" button that is located at the bottom of the Protocol Configuration, the dropdown of the new line will be in a state in which the last response on the Response List is selected. Thus, it will be automatically assigned as "TM—Stop". Once the "TM—Stop" response is added, the user will see that all the lines are in "white". This means that the protocol can be performed by the treadmill without any issues. Now the protocol is ready. The user should click the "Save" button to save the protocol inside the software. This action will close the Protocol Settings page and return to the main Protocols page. On the main Protocols page, there should be a protocol named "New Protocol" under the List of Protocols section.

In the illustrative embodiment, the user can edit a protocol after it has been created. To edit the protocol, the user clicks on the hamburger menu that is located at the top right corner of the protocol. From the hamburger menu, the user is able to do the following: (i) edit the protocol, which will open the Protocol Settings page; (ii) add the protocol to Favorites, which will mark that protocol as favorite; (iii) delete the protocol, which will remove the protocol from the List of Protocols and the software; and (iv) duplicate the protocol, which will create a clone of that protocol, which then later can be used to make minor adjustments without messing with the original.

In the illustrative embodiment, to perform a protocol, the protocol should be on the Queue that is located on both Protocols and the Workspace page (see e.g., FIGS. 2 and 7). The Queue acts like a playlist. To perform a protocol, the user should play the queue and the protocols located on there will start one by one following the list. To add a protocol to the Queue, the user just clicks twice on the protocol or clicks and drags the protocol over to the Queue and drops it therein. When a protocol is added to the Queue, it should be visible under the Queue section. The user can repeat the protocol by entering the number that he or she wants to repeat on the input field located on the protocol that is on the Queue. The user can also remove the protocol from the Queue by clicking the "X" button on it. The Queue is both on the Workspace and the Protocols page so that when the user creates the queue and makes changes to it on the Protocols page, the user can easily access it from the Workspace. Therefore, the user can see that the Queue on the Workspace page also has the protocol named "New Protocol" on the Queue.

In the illustrative embodiment, when there is a protocol in the queue, the user will see a play button being enabled at the bottom of the queue under both Protocols and the Workspace page. The user can start to perform the queue by clicking the Play button on either side. If the user clicks on the play button on the Protocols page, the Queue will start, and the screen will go to the Workspace page. If the user clicks on the Play button on the Workspace page, the Queue will start while remaining on the Workspace page. Initially, the user should click on the Play button located at the bottom of the screen. Then, after clicking the Play button, the user will see the Workspace page open, "New Protocol" added to the list, a green progress bar at the bottom of the protocol, the play button located at the bottom of the Queue turned into a Stop button, and a "Remaining Time" text visible at the bottom of the Queue. The user should also be able to see the changes on the treadmill as described above on the Data View and on the Treadmill controls. When the Queue is finished, the user will still see the "New Protocol" on the list, the Play button and all the device controls back to normal. The user can record this session simultaneously with the queue. In order to achieve this, the user goes to Capture Settings located at the bottom bar of the Workspace page. From here, the user fills out the File Name and the File Path fields. Then from the Sync Type dropdown, the user selects the Protocol option. This will allow the user to sync the recording with the Queue. Then, the user clicks the "Save" button, which saves the settings and closes the Capture Settings window. Then, the user clicks on the play button located at the bottom of the Queue. When the queue starts, in addition to the changes before, there is a progress bar located at the bottom bar, and a text that says "Recording" next to the recording icon and the name of the file should be visible under it. After the Queue stops, the user is able to see the captured data inside the user's designated folder with the assigned name.

Although the invention has been shown and described with respect to a certain embodiment or embodiments, it is apparent that this invention can be embodied in many different forms and that many other modifications and variations are possible without departing from the spirit and scope of this invention. Moreover, while reference is made throughout this disclosure to, for example, "an illustrative embodiment", "one embodiment" or a "further embodiment", it is to be understood that some or all aspects of these various embodiments may be combined with one another as part of an overall embodiment of the invention. Also, the compound conjunction "and/or" is used throughout this disclosure to mean one or the other, or both.

In addition, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:
1. A measurement and testing system, comprising:
at least one actuator, the at least one actuator configured to displace a surface on which a subject is disposed;
a visual display device having an output screen;

a user input device, the user input device configured to enable a user of the system to input or manipulate data; and at least one data processing device operatively coupled to the at least one actuator, the visual display device, and the user input device, the at least one data processing device including at least one hardware component, and the at least one data processing device configured to execute computer executable stored instructions, the computer executable stored instructions comprising instructions for:

generating a graphical user interface on the output screen of the visual display device, the graphical user interface including a device selection section with a plurality of different devices that are selectable by the user and a customizable device list that is configured to be populated by the user, the graphical user interface further including a protocol section, the protocol section comprising a protocol builder that enables the user to create and populate one or more customized protocols for selected ones of the plurality of different devices in the customizable device list, the one or more customized protocols comprising one or more device protocols with one or more actuator parameters for controlling the at least one actuator for a time period while the subject is disposed on the surface;

receiving one or more first input signals from the user input device for creating and populating the one or more customized protocols for the selected ones of the plurality of different devices in the customizable device list;

receiving a second input signal from the user input device that initiates an execution of one of the one or more device protocols for controlling the at least one actuator; and upon receiving the second input signal from the user input device, controlling the at least one actuator for the time period in accordance with the executed one of the one or more device protocols so as to displace the surface on which the subject is disposed in a prescribed manner.

2. The measurement and testing system according to claim 1, wherein at least one of the one or more device protocols displayed in the protocol section of the graphical user interface further comprise one or more device responses for automatically controlling the at least one actuator for the time period, each of the one or more device responses including a start time and an end time.

3. The measurement and testing system according to claim 2, wherein the plurality of different devices that are selectable by the user include at least a first device and a second device, and wherein the at least one actuator further comprises at least one first actuator of the first device and at least one second actuator of the second device, and the one or more device responses further comprise a first device response for automatically controlling the first actuator of the first device and a second device response for automatically controlling the second actuator of the second device.

4. The measurement and testing system according to claim 3, wherein the first device response and the second device response are executed simultaneously such that the first device and the second device are simultaneously displaced during a single predetermined time period.

5. The measurement and testing system according to claim 3, wherein the first device response and the second device response are executed sequentially such that the first device undergoes displacement initially during a first predetermined time period, followed by displacement of the second device during a second predetermined time period.

6. The measurement and testing system according to claim 3, wherein the first device is an instrumented treadmill and the at least one first actuator is an electric motor for rotating one or more belts of the instrumented treadmill; and wherein the second device is a motion base and the at least one second actuator is a motion base actuator for displacing the motion base.

7. The measurement and testing system according to claim 2, wherein the plurality of different devices that are selectable by the user include at least a first device, and wherein the at least one actuator further comprises at least one first actuator of the first device and at least one second actuator of the first device, and the one or more device responses further comprise a first device response for automatically controlling the first actuator of the first device and a second device response for automatically controlling the second actuator of the first device.

8. The measurement and testing system according to claim 7, wherein the first device response and the second device response are executed simultaneously such that the first device is simultaneously displaced by the at least one first actuator and the at least one second actuator during a single predetermined time period.

9. The measurement and testing system according to claim 7, wherein the first device response and the second device response are executed sequentially such that the first device undergoes displacement from the at least one first actuator initially during a first predetermined time period, followed by displacement from the at least one second actuator during a second predetermined time period.

10. The measurement and testing system according to claim 7, wherein the first device is an instrumented treadmill with incline adjustment and the at least one first actuator is an electric motor for rotating one or more belts of the instrumented treadmill and the at least one second actuator is a treadmill incline actuator for adjusting an inclination angle of the instrumented treadmill.

11. The measurement and testing system according to claim 1, wherein at least one of the one or more device protocols displayed in the protocol section of the graphical user interface further comprises a plurality of protocols arranged in a queue, and the at least one data processing device is further configured to execute computer executable stored instructions for:

receiving an input signal from the user input device that initiates an execution of a first one of the plurality of protocols arranged in the queue; and after completing the first one of the plurality of protocols, automatically executing each successive one of the plurality of protocols arranged in the queue.

12. The measurement and testing system according to claim 1, further comprising a measurement assembly having at least one measurement device, the at least one measurement device being configured to sense one or more measured quantities and output one or more signals that are representative of the one or more measured quantities, the at least one data processing device being further operatively coupled to the at least one measurement device of the measurement assembly, and the at least one data processing device being further configured to execute computer executable stored instructions for:

receiving the one or more signals that are representative of the one or more measured quantities and converting the one or more signals into output data; and displaying the output data in a portion of the graphical user interface on the output screen of the visual display device.

13. The measurement and testing system according to claim 12, wherein the at least one data processing device is further configured to synchronize a capture of the output data from the at least one measurement device of the measurement assembly with the execution of the one of the one or more device protocols resulting in a displacement of the surface on which the subject is disposed.

14. A measurement and testing system, comprising:
a measurement assembly having at least one measurement device, the at least one measurement device configured to sense one or more measured quantities and output one or more signals that are representative of the one or more measured quantities;
at least one actuator, the at least one actuator configured to displace a surface on which a subject is disposed;
a visual display device having an output screen;
a user input device, the user input device configured to enable a user of the system to input or manipulate data; and
at least one data processing device operatively coupled to the at least one measurement device of the measurement assembly, the at least one actuator, the visual display device, and the user input device, the at least one data processing device including at least one hardware component, and the at least one data processing device configured to execute computer executable stored instructions, the computer executable stored instructions comprising instructions for:
generating a graphical user interface on the output screen of the visual display device, the graphical user interface including a protocol section, the protocol section comprising one or more protocols with one or more actuator parameters for controlling the at least one actuator for a time period while the subject is disposed on the surface;
receiving an input signal from the user input device that initiates an execution of one of the one or more protocols for controlling the at least one actuator;
upon receiving the input signal from the user input device, controlling the at least one actuator for the time period in accordance with the executed one of the one or more protocols so as to displace the surface on which the subject is disposed in a prescribed manner;
receiving the one or more signals that are representative of the one or more measured quantities and converting the one or more signals into output data; and
displaying the output data in a portion of the graphical user interface on the output screen of the visual display device;
wherein at least one of the one or more protocols displayed in the protocol section of the graphical user interface further comprises a plurality of protocols arranged in a queue, and the at least one data processing device is further configured to execute computer executable stored instructions for:
receiving an input signal from the user input device that initiates an execution of a first one of the plurality of protocols arranged in the queue; and
after completing the first one of the plurality of protocols, automatically executing each successive one of the plurality of protocols arranged in the queue.

15. The measurement and testing system according to claim 14, wherein at least one of the one or more protocols displayed in the protocol section of the graphical user interface further comprises one or more device responses for automatically controlling the at least one actuator for the time period, each of the one or more device responses including a start time and an end time.

16. The measurement and testing system according to claim 15, wherein the at least one actuator further comprises at least one first actuator of a first device and at least one second actuator of a second device, and the one or more device responses further comprise a first device response for automatically controlling the first actuator of the first device and a second device response for automatically controlling the second actuator of the second device.

17. The measurement and testing system according to claim 16, wherein the first device response and the second device response are executed simultaneously such that the first device and the second device are simultaneously displaced during a single predetermined time period.

18. The measurement and testing system according to claim 16, wherein the first device response and the second device response are executed sequentially such that the first device undergoes displacement initially during a first predetermined time period, followed by displacement of the second device during a second predetermined time period.

19. The measurement and testing system according to claim 16, wherein the first device is an instrumented treadmill, the at least one first actuator is an electric motor for rotating one or more belts of the instrumented treadmill, and the measurement assembly is a part of the instrumented treadmill; and
wherein the second device is a motion base and the at least one second actuator is a motion base actuator for displacing the motion base.

20. The measurement and testing system according to claim 15, wherein the at least one actuator further comprises at least one first actuator of a device and at least one second actuator of the device, and the one or more device responses further comprise a first device response for automatically controlling the first actuator of the device and a second device response for automatically controlling the second actuator of the device.

21. The measurement and testing system according to claim 20, wherein the first device response and the second device response are executed simultaneously such that the device is simultaneously displaced by the at least one first actuator and the at least one second actuator during a single predetermined time period.

22. The measurement and testing system according to claim 20, wherein the first device response and the second device response are executed sequentially such that the device undergoes displacement from the at least one first actuator initially during a first predetermined time period, followed by displacement from the at least one second actuator during a second predetermined time period.

23. The measurement and testing system according to claim 20, wherein the device is an instrumented treadmill with incline adjustment, the at least one first actuator is an electric motor for rotating one or more belts of the instrumented treadmill, the at least one second actuator is a treadmill incline actuator for adjusting an inclination angle of the instrumented treadmill, and the measurement assembly is a part of the instrumented treadmill.

24. The measurement and testing system according to claim 14, wherein the at least one data processing device is further configured to synchronize a capture of the output data from the at least one measurement device of the measurement assembly with the execution of the one of the one or more protocols resulting in a displacement of the surface on which the subject is disposed.

25. A measurement and testing system, comprising:

a force measurement assembly having a surface on which a subject is configured to be disposed, the force measurement assembly including at least one force transducer that is configured to sense one or more measured quantities and output one or more signals that are representative of forces and/or moments being applied to the force measurement assembly by the subject;

a visual display device having an output screen;

a user input device, the user input device configured to enable a user of the system to input or manipulate data; and at least one data processing device operatively coupled to the at least one force transducer of the force measurement assembly, the visual display device, and the user input device, the at least one data processing device including at least one hardware component, and the at least one data processing device configured to execute computer executable stored instructions, the computer executable stored instructions comprising instructions for:

generating a graphical user interface on the output screen of the visual display device, the graphical user interface including a protocol section, the protocol section comprising one or more protocols related to the measurement assembly;

receiving an input signal from the user input device that initiates an execution of one of the one or more protocols;

receiving the one or more signals that are representative of the forces and/or moments being applied to the force measurement assembly by the subject and converting the one or more signals into output force and/or moment data; and displaying the output data in a portion of the graphical user interface on the output screen of the visual display device.

26. The measurement and testing system according to claim 25, wherein the force measurement assembly is in a form of a (i) force plate or (ii) an instrumented treadmill.

* * * * *